US008948851B2

(12) United States Patent
Leblond et al.

(10) Patent No.: US 8,948,851 B2
(45) Date of Patent: Feb. 3, 2015

(54) METHOD AND APPARATUS FOR DEPTH-RESOLVED FLUORESCENCE, CHROMOPHORE, AND OXIMETRY IMAGING FOR LESION IDENTIFICATION DURING SURGERY

(75) Inventors: Frederic Leblond, West Lebanon, NH (US); David W. Roberts, Lyme, NH (US); Brian W. Pogue, Hanover, NH (US); Keith D. Paulsen, Hanover, NH (US); Alex Hartov, Enfield, NH (US); Scott C. Davis, Woodsville, NH (US); Dax Kepshire, West Lebanon, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 164 days.

(21) Appl. No.: 13/145,505

(22) PCT Filed: Dec. 4, 2009

(86) PCT No.: PCT/US2009/066839
§ 371 (c)(1),
(2), (4) Date: Jul. 20, 2011

(87) PCT Pub. No.: WO2010/090673
PCT Pub. Date: Aug. 12, 2010

(65) Prior Publication Data
US 2011/0275932 A1    Nov. 10, 2011

Related U.S. Application Data

(60) Provisional application No. 61/145,900, filed on Jan. 20, 2009.

(51) Int. Cl.
*A61B 6/00* (2006.01)
*A61B 6/02* (2006.01)
(Continued)

(52) U.S. Cl.
CPC ............ *A61B 5/0073* (2013.01); *A61B 5/0062* (2013.01);
(Continued)

(58) Field of Classification Search
None
See application file for complete search history.

(56) References Cited

U.S. PATENT DOCUMENTS 5,109,276 A * 4/1992 Nudelman et al. .............. 348/47
6,175,759 B1   1/2001 Chan et al.
(Continued)

FOREIGN PATENT DOCUMENTS

JP    2006195240 A    7/2006
WO   2005089637 A2   9/2005

OTHER PUBLICATIONS

Patwardhan S, Monte Carlo Simulation of Light-Tissue Interaction: Three-Dimensional Simulation for Trans-Illumination-Based Imaging of Skin Lesions, IEEE Transactions on Biomedical Engineering, vol. 52, No. 7, Jul. 2005, pp. 1227-1236.*

(Continued)

*Primary Examiner* — Long V. Le
*Assistant Examiner* — Bradley Impink
(74) *Attorney, Agent, or Firm* — Lathrop & Gage LLP

(57) ABSTRACT

A tomographic fluorescent imaging device for imaging fluorophores in biological tissues has a scanned laser for scanning the tissue and a camera for receiving light from the biological tissue at an angle to the beam at a second wavelength ten or more nanometers greater in wavelength than the wavelength of the laser. Use of both intrinsic and extrinsic fluorophores is described. Images are obtained at each of several positions of the beam. An image processing system receives the series of images, models a path of the beam through the tissue, and determines depth of fluorophore in tissue from intersections of the modeled path of the beam and the path of the received light. The laser is of 600 nm or longer wavelength, to provide penetration of tissue. The imaging device is used during surgery to visualize lesions of various types to ensure complete removal of malignant tumors. An alternative embodiment uses differences in intensity of fluorescent radiation from tissue as observed at different wavelengths to determine depth of fluorophore in tissue. An embodiment operates at multiple wavelengths to construct tomographic images of chromophores, such as hemoglobin, and is capable of dynamic imaging.

20 Claims, 11 Drawing Sheets

(51) Int. Cl.
  *A61B 5/00* (2006.01)
  *G02B 21/00* (2006.01)
  *G02B 21/16* (2006.01)
  *A61B 19/00* (2006.01)

(52) U.S. Cl.
  CPC .......... *A61B 5/416* (2013.01); *G02B 21/0064* (2013.01); *G02B 21/16* (2013.01); *A61B 19/5223* (2013.01); *A61B 19/5244* (2013.01)
  USPC .............. 600/476; 600/473; 850/31; 356/611

(56) References Cited

U.S. PATENT DOCUMENTS

| | | | |
|---|---|---|---|
| 6,208,886 | B1 | 3/2001 | Alfano et al. |
| 6,661,571 | B1* | 12/2003 | Shioda et al. ................. 359/372 |
| 7,804,075 | B2* | 9/2010 | Ntziachristos et al. .... 250/458.1 |
| 2004/0015062 | A1* | 1/2004 | Ntziachristos et al. ....... 600/312 |
| 2005/0085732 | A1* | 4/2005 | Sevick-Muraca et al. .... 600/473 |
| 2007/0038126 | A1* | 2/2007 | Pyle et al. .................... 600/476 |
| 2007/0083124 | A1 | 4/2007 | Ehben et al. |
| 2007/0145136 | A1* | 6/2007 | Wiklof et al. ................. 235/454 |
| 2007/0238957 | A1 | 10/2007 | Yared |
| 2008/0218727 | A1* | 9/2008 | Djeziri et al. ..................... 356/2 |
| 2008/0267472 | A1 | 10/2008 | Demos |
| 2009/0137908 | A1* | 5/2009 | Patwardhan ................. 600/476 |
| 2009/0295910 | A1* | 12/2009 | Mir et al. ........................ 348/61 |
| 2011/0183370 | A1 | 7/2011 | Noiseux et al. |
| 2012/0133740 | A1 | 5/2012 | Klimov et al. |

OTHER PUBLICATIONS

International Search Report and Written Opinion issued in related PCT Patent Application Serial No. PCT/US2009/066839, Jun. 25, 2010, 11 pages.

International Search Report and Written Opinion issued in related PCT Patent Application Serial No. PCT/US2014/016291, dated May 27, 2014, 13 pp.

* cited by examiner

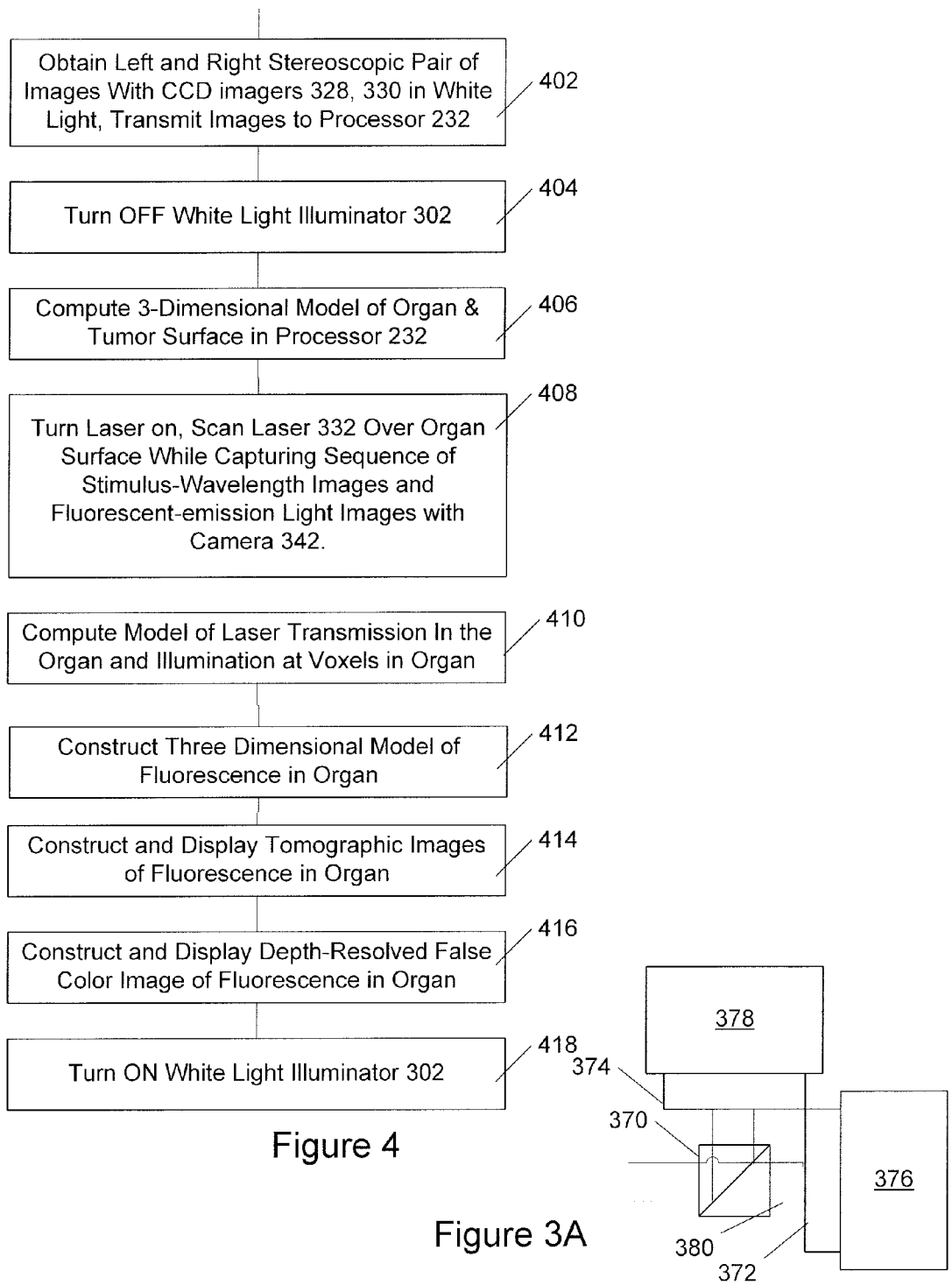

METHOD AND APPARATUS FOR DEPTH-RESOLVED FLUORESCENCE, CHROMOPHORE, AND OXIMETRY IMAGING FOR LESION IDENTIFICATION DURING SURGERY

RELATED APPLICATIONS

The present application claims priority from U.S. Provisional Patent Application No. 61/145,900 filed Jan. 10, 2009, the disclosure of which is incorporated herein.

GOVERNMENT RIGHTS

The work discussed herein has been supported by the National Institutes of Health and National Institute of Neurological Diseases and Stroke grant number 1R01NS052274-01A2. The United States Government has certain rights in this invention.

FIELD

The present application relates to the fields of surgical microscopes and surgery. In particular, it relates to apparatus, compounds, and methods for using fluorescent-tagging pharmaceuticals, including prodrugs, to provide enhanced contrast between normal and abnormal tissue, and for resolving tagged tissue with depth-resolved fluorescence microscopy during surgery.

BACKGROUND

There are many types of lesions treatable with surgical removal or modification. These lesions include tissues abnormal for any location in the body, such as malignant (or cancerous) tumors, and many slower-growing "benign" tumors. These lesions also include tissues that are abnormal for their location in a particular organ, but resemble normal tissues found in other locations in the body. Other lesions may incorporate material foreign to the body, including bacteria, viruses, or parasites, and associated zones of immune reactions. Still others involve developmental anomalies, such as arteriovenous malformations and berry aneurisms. Other lesions may incorporate scars and adhesions from prior illness or injury. While lesions are of many kinds, it is generally desirable for a surgeon to be able to visualize the lesion being treated and to be able to discriminate between normal and lesion tissues.

Many tumors and other lesions do not have a capsule or other connective tissue that separates them from nearby normal tissues, they may have irregular boundaries. Invasive malignant tumors in particular often have infiltrations and filaments containing malignant cells that penetrate into adjacent normal tissue. Some tumor types, including gliomas, have motile cells that may migrate a short distance away from the tumor into normal tissue; once these cells have found a hospitable location they may grow and form a new spinoff tumor. The new tumor may or may not become attached to the parent tumor, if it becomes attached it may resemble a filament of tumor. Either way, the tumor may develop a somewhat ragged edge with filaments and spots penetrating into adjacent tissue.

To reduce recurrence of many tumors, including many malignancies, after surgical treatment, it is considered desirable to remove all detectable portions of the tumor.

While filaments of tumor, and motile cells, may stop extending for a time when they reach an organ capsule, resulting in tumor encapsulated in the organ, it is often undesirable to remove an entire organ or organ lobe—especially when an organ is critical for life and the tumor may not have invaded the entire organ. For example, removal of more brain tissue or spinal cord than necessary can cause life-altering neurological impairment. Similarly, it may be desirable to save as much as possible of a patient's only kidney. There are other organs and body structures where tumors may form but where it may be desirable to retain as much post-surgery organ structure and function as possible.

These invasive portions of tumors may not be readily visible to a surgeon—even under magnification. Other lesion types may also have portions that have color and structure that resemble nearby healthy tissue.

A prior method of ensuring complete tumor removal while retaining as much organ as possible involves a pathologist cooperating with the surgeon. The surgeon removes the tumor and some adjacent tissue, while the pathologist immediately examines frozen sections to verify that the removed tissue includes a tumor-free margin. Should tumor portions be found to extend to boundaries of the removed tissue, extension of tumor beyond the removed tissue is assumed and more adjacent tissue is removed before closing the incision. This method tends to be slow, requiring extended anesthesia times and repeated frozen sections, and may require removal of more tissue that necessary because frozen sections can only be performed on tissue after the tissue is removed from the patient. Further, not all abnormal tissue types are readily distinguished in a frozen section. An alternative or supplemental method involves pathological examination of stained sections to verify complete tumor removal with removal of adequate margins of healthy tissue, however stained sections often take so much time to prepare that any further removal requires re-operation.

It is desirable to find improved ways of locating and identifying abnormal, abnormal for the organ, and malignant tissue, including small invasive branches of tumors, in tissue adjacent to tumors, during surgery.

Generally, surgeons treat lesions that are visible to them during surgery. At times, lesions and tumors may lie under the surface of an organ, or under a visible and exposed surface of an operative site, where they may be obscured by overlying tissue and not readily visible. It is desirable to make these lesions, including portions of malignant tumors, visible to a surgeon so that they can be more readily treated, with less normal overlying tissue damaged during treatment, than with current techniques. It is therefore also desirable to visualize malignant tissue or other lesions that may lie below the surface of an organ during surgery.

It is known that some fluorescent compounds will accumulate in tumors and other abnormal tissues. Further, it is known that some prodrugs, such as 5-aminolevulinic acid (5-ALA) can be metabolized into fluorescent compounds to a greater extent in some tumor tissues than in surrounding normal stroma. Marking of tumors with 5-ALA metabolites and using resultant fluorescence at the surface of an operative site to guide surgery has been reported in the literature. For example Stummer, et al., Fluorescence-guided surgery with 5-aminolevulinic acid for resection of malignant glioma: a randomized controlled multicentre phase III trial, Lancet Oncology, Lancet Oncology, Lancet Oncol., 2006. 7(5): p. 392-401, published online Apr. 13, 2006 at ncology.thelancet.com, reports that removal of malignant glioma tumor tissue marked with fluorescent metabolites of 5-ALA and fluorescing in the visible spectrum at the surface of an operative site under violet-blue excitation light during surgical treatment of glioma enhanced survival in human subjects.

Similar studies have also been performed in mice. It is expected that these results may apply for other lesion types.

Experiments have been previously conducted with tomographic fluorescent imaging of concentrations of fluorescent compounds, or fluorophores, in biological tissues. Vasilis Ntziachristos and Ralph Weissleder, Charge-coupled-device based scanner for tomography of fluorescent near-infrared probes in turbid media, Medical Physics, Vol. 29, No. 5, May 2002, have reported a use of diffuse optical tomography in "small animal geometries". The device of Ntziachristos and Weissleder, however, operates in a transmission mode. In transmission mode, light is transmitted light into turbid medium, and emitted light is detected from several points on the surface, including points on an opposite side of the turbid medium from the points where light is applied. The turbid medium of Ntziachristos and Weissleder is about one inch thick, far thinner than many human organs and tissues, because it is used in small animals such as laboratory mice. The device of Ntziachristos and Weissleder applies light to the medium from a pulsed laser, and detects light from the medium, through an arrangement of optical fibers placed about the medium. The device of Ntziachristos and Weissleder uses an intensified charge-coupled device (ICCD) camera to time-resolve the detected fluorescence in a time-domain system. Additional devices for optical imaging of biological tissues have been reported in Hillman, E., *Optical brain imaging in vivo: techniques and applications from animal to man*. Journal of Biomedical Optics, 2007. 12(5): p. 051402.

Frederic Leblond, et al, *Diffuse optical fluorescence tomography using time-resolved data acquired in transmission*, in Multimodal Biomedical Imaging II, vol. 6431. Proceedings of the International Society of Optical Imaging (2007) disclosed a time-dependent method for solving the diffusion equation (DE) for light propagation in tissues, and reconstruction algorithms for use therewith.

US Patent application 20080218727, to Djeziri, et al., entitled Method And Apparatus For Optical Image Reconstruction Using Contour Determination, 2008, describes the importance of determining tissue contours and the impact of tissue contour in diffuse optical tomography reconstruction algorithms in context of intact breast imaging. Djeziri proposes raster-scanning to determine an intensity profile, and using the intensity profile as a surface contour of the breast. He specifies using an optical fluid to fill space between the breast surface and the optical fibers of his diffuse optical tomography apparatus during diffuse optical imaging.

During surgery, use of an optical fluid to fill space between transmit and receive optical fibers is often difficult because this fluid would need to fill the surgical wound, could infiltrate into the patient, and may require a dam around the wound. Further, operation of a diffuse optical imager in transmission mode may prove difficult if the body part being operated upon is thicker than an inch—as are the brain, kidneys, and many other organs.

Most tissues of the human body are soft tissues; these tissues are inherently flexible and readily deformable. Further, many of these soft tissues interface with other tissues along boundaries where considerable movement may take place. During surgery, as adjacent structures such as skin, muscle, and bone are moved and pressure applied to soft tissues with instruments such as retractors, these tissues will deform and shift. Since these tissues may deform readily both between imaging and surgery, and during surgery, it is common for surgeons to find lesions, including tumors and foreign objects, and other surgical targets are no longer in the exact positions they occupied in preoperative images.

For a surgeon to properly treat these lesions, the surgeon must locate them during surgery. Further, for surgeons to avoid unintended damage to other nearby structures, it may also be necessary to locate particular portions of those other structures precisely during the surgery.

MRI and CT imaging are often used to provide high resolution preoperative images of surgical targets. The equipment required to make these images is bulky, expensive, and not easily incorporated into an operating-room environment. Further, the intense magnetic fields required for MRI may be incompatible with other operating room instruments and equipment, and radiation emitted by CT machines may require surgeon and staff wear bulky and heavy lead-lined garments or leave the room during intraoperative imaging.

In Hartov, et al., Error Analysis for a Free-Hand Three Dimensional Ultrasound System for Neuronavigation, Neurosurgical Focus 6 (3), 5 Aug. 1999, it was suggested that sensors produced by Ascension Technology Corporation, Milton, Vt., be used to track a handheld ultrasound transducer in three dimensions. An alternative system uses a Stealthstation® 3-D surgical navigation system produced by Medtronic, of Minneapolis, Minn., for tracking instruments in three dimensions relative to a patient during surgery.

There are also chromophores naturally present in biological tissues, including human tissue. A leading such chromophore is the iron-containing heme group—as found in myoglobin and hemoglobin. Heme is generally found in both oxygenated and un-oxygenated forms in the body, it is well known that absorption spectra of heme differs between the oxygenated and un-oxygenated forms; this difference in absorption may be used to identify tissues having different oxygen concentrations.

Many malignant tumor types have high metabolic activity due to rapid cell division and growth. These tumors often outgrow the local oxygen supply; some tumors stimulate rapid proliferation of blood vessels to overcome this, and some tumors develop core areas of low oxygen tension and may develop necrotic portions. Imaging of heme concentrations and oxygenation may assist in locating some types of malignant tumor tissue, as well as of imaging tissues such as muscle, bone marrow, liver, spleen, and blood vessels including arteriovenous malformations and aneurysms that naturally have high heme concentrations. Djeziri's diffuse optical imaging system of the breast described above is intended to visualize heme concentrations, such as those that result from rapid blood-vessel proliferation.

Muscle, including cardiac muscle, and brain activities are known to consume oxygen. A normal physiological response to this increase of oxygen consumption with activity is to dilate blood vessels to increase blood flow in affected tissue. In many diseases, including peripheral vascular disease, and cardiovascular disease, as well as cerebrovascular disease, ischemic bowel disease, and other conditions, this physiological increase of flow is impaired resulting in a greater than normal local decrease in oxygenation of heme. A significant decrease in oxygenation may produce pain or other signs and symptoms, as in intermittent claudication or angina. Further, mapping increases in blood flow can be of interest in monitoring activity in the brain.

For all these reasons, it is desirable to be able to map areas of heme concentration, to map areas of oxygenated heme and deoxygenated heme, and to be able to view dynamic changes in oxygenation with tissue activity.

Other chromophores naturally present in some tissues, including some types of tumor tissues, are naturally fluorescent.

Swartling, et al. Fluorescence spectra provide information on the depth of fluorescent lesions in tissue, Optics Letters, 2005, 44(10) pp 1934-1941 found that emissions from fluorophores have spectra that depend on the depth of the fluorophores.

SUMMARY

A tomographic fluorescent imaging device for imaging fluorophores in biological tissues has a scanned laser for scanning the tissue and a camera for receiving light from the biological tissue at an angle to the beam at a second wavelength ten or more nanometers greater in wavelength than the wavelength of the laser. Multiple images are obtained at multiple positions of the beam. An image processing system receives the series of images, models a path of the light through the tissue, and determines depth of fluorophore in tissue from intersections of the modeled light paths and the path of the received light. The modeled path incorporates modeling of photon scattering and absorption in the diffuse media of the tissue.

A method of constructing a tomographic fluorescent image requires scanning a beam of light into tissue, while an image processor models a path of light of the beam in the tissue. Fluorescent light is received at a second wavelength on a path at an angle to the beam; multiple images are captured to show fluorescent regions at different beam positions in the media. These images are used to reconstruct an array of voxels, modeling illumination of voxels by the beam as it scatters into the tissue. Fluorescence at each voxel and scattering of fluorescent light is then modeled while fitting the fluorescence parameter at voxels to the captured images. Determined florescence at the voxels is then displayed as a tomographic image. In some but not all particular embodiments, the absorbance and scattering parameters of the model are also refined at each voxel to match the experimental data, and in those embodiments these refined parameters may also be displayed.

A method of performing surgery to remove a tumor from a human subject includes administering a prodrug metabolized in the tumor to a greater degree than in normal tissue, the prodrug being metabolized to a fluorescent molecule, exposing an organ, and scanning a beam of light into the organ. A modeling and image processor models a path of the beam in the organ, and fluorescent light emitted by the fluorescent molecule as excited by light of the beam is imaged on a path at an angle to the beam at multiple positions of the beam. The received fluorescent light is used to determine intensity of voxels of an array of voxels, modeling illumination of voxels by the beam as it scatters into the tissue. Fluorescence at each voxel and scattering of fluorescent light is then modeled while fitting the fluorescence at voxels to the captured images. Determined florescence at the voxels is then displayed as a tomographic image. Information from the voxels is displayed to a surgeon; and tissue having high fluorescence is removed from the organ. The method is particularly applicable to removing glioma from brain.

An alternative embodiment of the method of performing surgery to remove a tumor from a human subject includes exposing an organ, and scanning a beam of light into the organ. A modeling and image processor models a path of the beam in the organ, and fluorescent light emitted by fluorescent chromophores naturally occurring in the tumor and excited by the beam is imaged on a path at an angle to the beam at multiple positions of the beam. The received fluorescent light is used to determine intensity of voxels of an array of voxels, modeling illumination of voxels by the beam as it scatters into the tissue. Fluorescence at each voxel and scattering of fluorescent light is then modeled while fitting the fluorescence at voxels to the captured images. Determined florescence at the voxels is then displayed as a tomographic image. Information from the voxels is displayed to a surgeon; and tissue having high fluorescence is removed from the organ. The method is particularly applicable to removing glioma from brain.

Another embodiment of the tomographic optical imaging device has a light source for providing filtered stimulus light to tissue, an objective lens, a low-pass wavelength-selective device for passing fluorescent light, and a beamsplitter disposed between the objective lens and an eyepiece for diverting at least a portion of the fluorescent light into a rotary filter. The rotary filter has two bandpass elements having different center wavelengths in a wavelength band of the fluorescent light, and passes light to an electronic camera. An image processing system is provided for receiving images from the electronic camera, and for computing depth of fluorophore in tissue at pixels of images based on differences between intensity of fluorescent light passed by the bandpass elements at different wavelengths and for displaying the computed depth of fluorophore to a surgeon. This embodiment operates on the principle that fluorescent light passed through significant depths of tissue has different spectral characteristics than fluorescent light as emitted by a fluorophore located, for example, directly on the tissue surface.

BRIEF DESCRIPTION OF THE FIGURES

FIG. 3A illustrates an alternative high resolution camera for the optical path of FIG. 3.

FIG. 4 is a flow chart of the method of depth resolution of fluorescence.

DETAILED DESCRIPTION OF THE EMBODIMENTS

Figure 1:
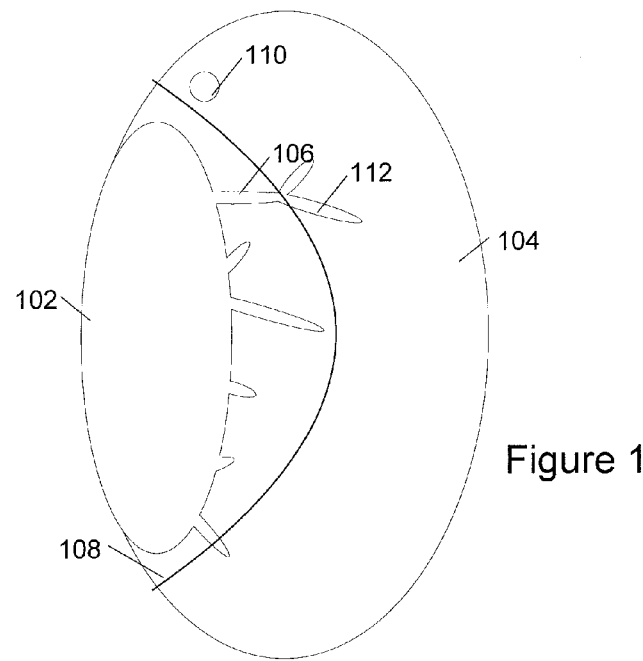
FIG. 1 is an illustration of an invasive tumor.

A cross section of a lesion 102, such as a malignant tumor, in an organ 104 is illustrated in FIG. 1. The lesion 102 has some invasive filaments 106 that penetrate deep into organ 104. If a surgeon operates on the tumor, removing tissue along a cut line 108, some portions of tumor may remain in organ 104, including new spinoff tumor 110 developed from motile cells of the parent tumor, and portions of invasive filaments 112. Either remaining tumor portion 110, 112 may grow and cause harm to the patient; it is desirable to locate and remove these portions to ensure optimum patient survival.

Figure 2:
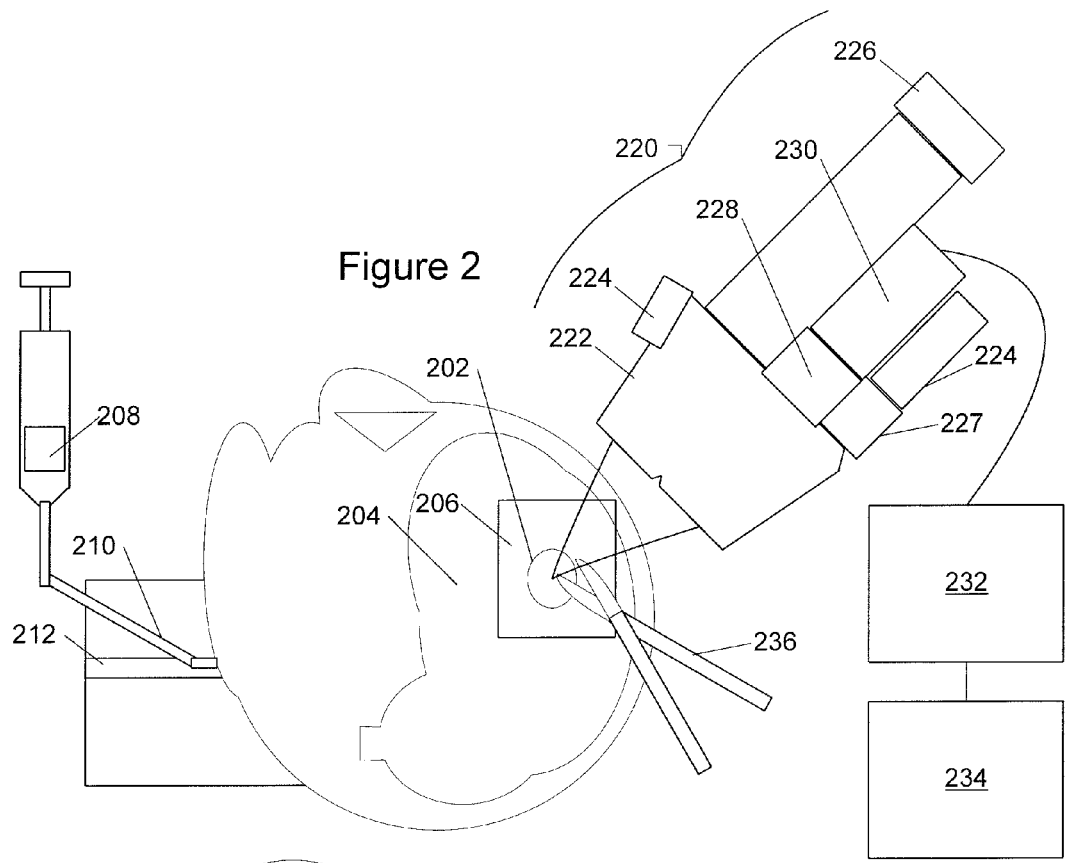
FIG. 2 illustrates a new method of resolving tumor boundaries during surgery.

A new method of treating lesion such as an invasive tumor 202 (FIG. 2), for example a glioma, is applicable to tumors located in an organ 204, such as brain, where treatment by removal of the entire organ is undesirable; particular embodiments of the method are applicable to many other lesion types, some examples of which are also explained herein.

The tumor 202 is exposed through an incision 206, and for glioma a craniotomy, as known in the art of surgery. A contrast enhancing dye 208 is injected through a catheter 210 that has been positioned into an artery 212, such as a branch of a carotid artery that provides circulating blood to tumor 202 and surrounding tissue of organ 204. The contrast enhancing dye 208 is chosen such that dye 208 is fluorescent and preferentially accumulates in the tumor to a greater extent than in surrounding organ 204; or a fluorescent metabolite of contrast enhancing dye 208 preferentially accumulates in the tumor 202. In some embodiments, dye 208 contains a prodrug that is metabolized by some tissues into fluorescent molecules and is not fluorescent by itself. In other embodiments, dye 208 contains an antibody bound to a fluorescent molecule; in these embodiments the antibody preferentially accumulates in the tumor with result that the fluorescent molecule also preferentially accumulates in the tumor.

The route, and timing, of administration of dye 208 is determined as appropriate for the particular dye, and the condition of the subject. The prodrug 5-AminoLevulinic Acid may be administered orally or by injection. Other dyes 208, such as antibodies bound to fluorescent molecules, may require injection.

In an embodiment, dye 208 contains indocyanine green. This dye is largely retained in blood vessels by the tightly adherent epithelial cells of capillaries often referred to as the "blood-brain barrier" in normal brain. Indocyanine green (ICG) leaks from capillaries into some types of tumor tissue; in some tumors this leakage into tumor may be because the epithelial cells are not as tightly adherent to each other in tumor as in normal brain—the "blood-brain barrier" is disrupted in tumor. Prior studies also show accumulation of ICG fluorophore in tumor tissue, as reported by Ntziachristos, V., et al., *Concurrent MRI and diffuse optical tomography of breast after indocyanine green enhancement*, Proceedings of the National Academy of Sciences of the United States of America, 2000. 97(6): p. 2767-72.

In another embodiment, dye 208 incorporates a fluorescein-based dye. Fluorscein has been reported as concentrating preferentially in tumor tissue by Kuroiwa, T., Y. Kajimoto, and T. Ohta, *Development of a fluorescein operative microscope for use during malignant glioma surgery: a technical note and preliminary report*. Surgical Neurology, 1998. 50(1): p. 41-8; discussion 48-9.

In another embodiment, dye 208 comprises the prodrug 5-AminoLevulinic Acid (5-ALA). 5-ALA has been previously administered to humans, for example in studies of phototherapy for Barrett's esophagus. 5-ALA dye is not fluorescent by itself, but in some tissue types, including some tumor tissues, may be metabolized into protoporphyrin IX, which is fluorescent. Prior studies, such as Friesen, et al., 5 *Aminolevulinic Acid-Base Photodynamic Detection And Therapy Of Brain Tumors*, International Journal Of Oncology, vol 21, no. 3, 577-82 (September 2002) as well as the previously cited report by Stummer show preferential accumulation of protoporphyrin IX in glioma tissue, including glioblastoma and meduloblastoma tissue, following 5-ALA administration to a subject having a tumor. The tumor tissue accumulates a greater concentration of the protoporphyrin IX than does surrounding normal brain tissue. Tumors were observed in mice to have up to ten times greater concentration of protoporphyrin IX in tumor as compared to nearby normal brain tissue four hours after administration of 100 milligrams per kilogram of body weight of 5-ALA. Similarly, aluminum phtalocyanine is a fluorescent dye that has been shown in vivo to have accumulated in tumor to a concentration nearly four times that in normal tissue some fifty hours after administration.

A phase-3 human trial of surface fluorescent microscopy during surgical removal of malignant tumors marked with 5-ALA showed increased survival following surgery when all fluorescent tumor visible at excision cavity surfaces are removed; see Stummer, et al., *Fluorescence-guided surgery with 5-aminolevulinic acid for resection of malignant glioma: a randomized controlled multicentre phase III trial*, Lancet Oncol., 2006. 7(5): p. 392-401, published online at oncology.thelancet.com. Additional phase 3 studies using a surface fluorescence microscope to identify, and remove, all tumor marked by administering 20 milligrams per kilogram 5-ALA to each subject are underway. These studies compare survival in human subjects between conventional surgery and conventional surgery followed by removal of tumor portions fluorescing under blue light at surfaces of the excision cavity.

5-ALA may also be usable to locate tumors in other organs. In particular, 5-ALA has been shown to be preferentially metabolized into protoporphyrin IX in tumors of the prostate as compared to protoporphyrin IX production in surrounding normal prostate tissue. This may offer the opportunity to remove the prostate tumors with reduced risk of damaging nerves responsible for penile sensation and erection; thereby preserving functions thought important by many patients.

In yet another embodiment, dye 208 contains a fluorescent molecule or prodrug metabolized into fluorescent molecules in-vivo that is attached to a monoclonal antibody having specificity for tumor tissue.

In an embodiment tailored for use with tumors 202 metastatic from a distant organ (not shown) such as lung, dye 208 comprises a fluorescent molecule or prodrug attached to an antibody, such as a monoclonal antibody, having specificity towards a tissue type of the distant organ. Because many metastatic tumors 202 retain some cell-surface markers similar to those of the parent tissue, dye 208 preferentially delivers the fluorescent molecule or prodrug to the tumor 202 tissue, while delivering a substantially lower concentration of the fluorescent molecule or prodrug to the organ 204.

A surgeon visualizes the tumor through a fluorescent tomographic surgical microscope 220 having several modes of operation as detailed below.

Microscope 220 has a first mode for imaging in white light. Microscope 220 has a second mode for imaging fluorescence at the surface of tissue. Microscope 220 has a third mode for tomographic imaging of fluorescence beneath the surface of tissue as well as at the surface of tissue.

The fluorescent tomographic microscope 220 has a lens system 222. In the first mode, the tumor 202 and adjacent organ 204 are illuminated by a traditional white-light illuminator 224, such as a white light emitting diode (LED), a halogen incandescent lamp, or other light source, from which white light is transmitted to the tumor 202 and organ 204. The lens system 222 is coupled to eyepieces 226 for viewing the tumor 202 under magnification and to electronic cameras 230 for capturing images of the tumor 202.

Figure 11:
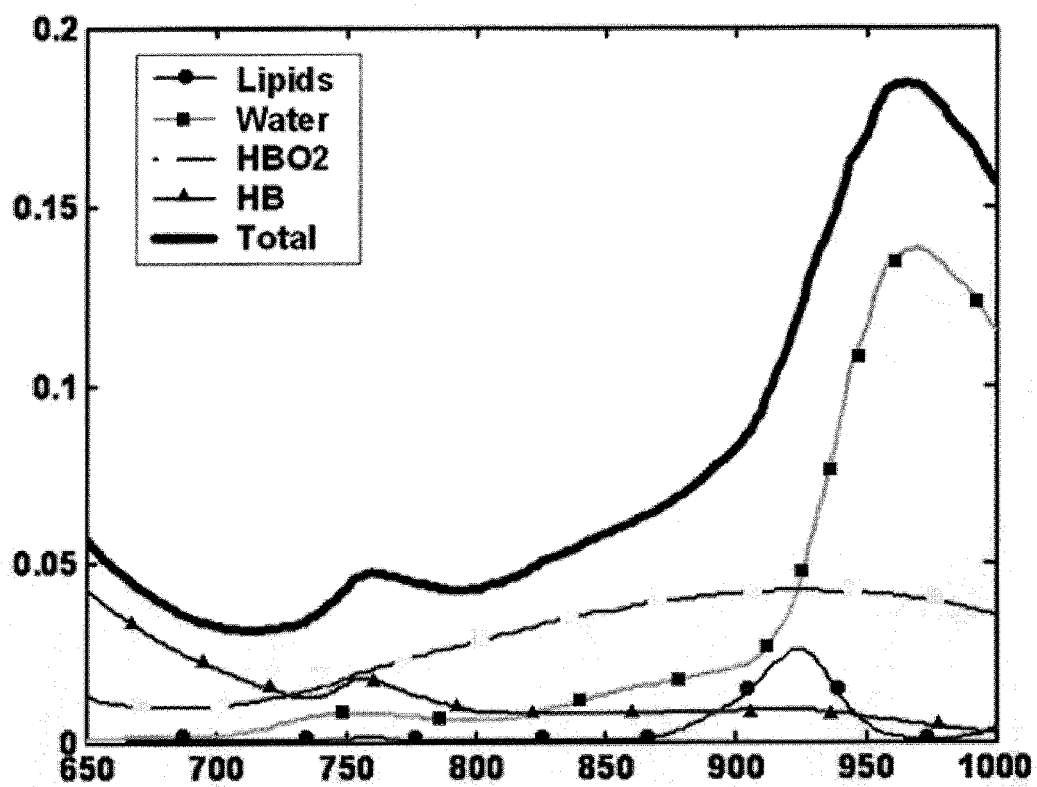
FIG. 11 illustrates absorption of various tissue components at various wavelengths of light.

Typically, tumors and organs are light propagation media where absorption and scattering is particularly important at short wavelengths, making them seem opaque to visible light. Consequently the white light images give good resolution but do not give good visibility of features beneath a surface of the tissue of tumor and organ. In particular, light at the blue end of the visible spectrum is often absorbed and scattered within less than a millimeter of the surface, rendering it difficult to see deeper structures. Further, because fine invasions of tumor may have color and structure superficially resembling that of surrounding tissues, these fine invasions of tumor at the surface may not be readily visible to the surgeon. However, the interaction of far-red and near-infrared light with biological tissue is such that propagation is inherently different when compared to that of visible light. For far-red and near-infrared light, scattering is still important but absorption by the main contributing chromophores such as hemoglobin and water are dramatically reduced (see FIG. 11). This provides an opportunity for imaging structures embedded deeper into the tissue using far-red and near-infrared light.

In the second mode, the tumor 202 and adjacent portions of organ 204 are illuminated by a primarily monochromatic illuminator, such as monochromatic LEDs. Alternatively, a combination of a filter for creating mainly-monochromatic light by filtering white light, and a white light source such as a halogen incandescent lamp or a high-intensity discharge lamp, may be used. Since this monochromatic illuminator is not scanned like the laser of the third mode and instead has a broad beam simultaneously illuminating much or all of exposed organ 204, it may be referred to as a monochromatic flood illuminator. Light from the monochromatic illuminator is transmitted to the tumor 202 and organ 204. The lens system 222 is coupled to eyepieces 226 for viewing the tumor 202 under magnification, and a filter may be used to enhance contrast by making fluorescent light from the tumor 202 and organ 204 surfaces more apparent by passing light at wavelengths of the fluorescent emitted light while blocking light at wavelengths emitted by the monochromatic illuminator.

When used with blue or green light, this second mode provides visibility of fluorescent-labeled tumor at the surface of organ 204 or tumor 202 with fluorophores that emit in visible wavelengths, such as protoporphyrin IX, concentrated in tumor.

In an alternative embodiment, the monochromatic illuminator provides red or near infrared light between 600 and 1000 nanometers wavelengths, this light is capable of deeper penetration into organ and tumor than blue or green light and is within the range of wavelengths that can be detected by available electronic cameras. The wavelength used is chosen to be appropriate for the fluorophore used to label the organ or tumor. In this mode, an appropriate filter 340 (FIG. 3) and camera 342 can provide fluorescence information coming from greater depths in the organ 204 or tumor 202. This provides the surgeon with non depth-resolved information pertaining to the fluorophore distribution beneath the surface; this information may be somewhat hazy due to scattering in the tissue.

In an embodiment, multiple monochromatic illuminators are provided, and multiple filters 340 are provided, permitting rapid selection of surface and deep imaging wavelengths, and wavelengths suitable for different fluorophores.

In the third, fluorescence-tomographic imaging, mode, the tumor 202 and adjacent organ tissue 204 may be illuminated by light from laser 224 through a biaxial scanning mirror 227 subsystem; this light is transmitted to the tissue 204 and tumor 202 by portions of lens system 222. At least some light from lens system 222 is coupled through other optical components 228 to a camera of cameras 230. Information from the cameras 230 is passed to an image processing subsystem 232 and fluorescence image information is displayed to the surgeon on an image display device 234. The fluorescence image information provides information of location and depth of concentrations of fluorescent molecules from dye 208 in tumor 202 and organ 204.

The surgeon views the fluorescence image information on display device 234 before, after, or at intervals while using surgical instruments such as surgical scissors 236, cryocautery devices (not shown), and electrocautery devices (not shown) to remove or destroy part or all of tumor 202.

When the surgeon wants to determine if any tumor tissue, such as tumor portions 110 & 112 with reference to FIG. 1, remains in the organ 204, including beneath the surface of organ 204, the surgeon triggers the fluorescent tomographic microscope 220 to obtain new fluorescence tomographic image information, views that information of display device 234, and may remove additional portions of tumor 202 and organ 204.

Figure 3:
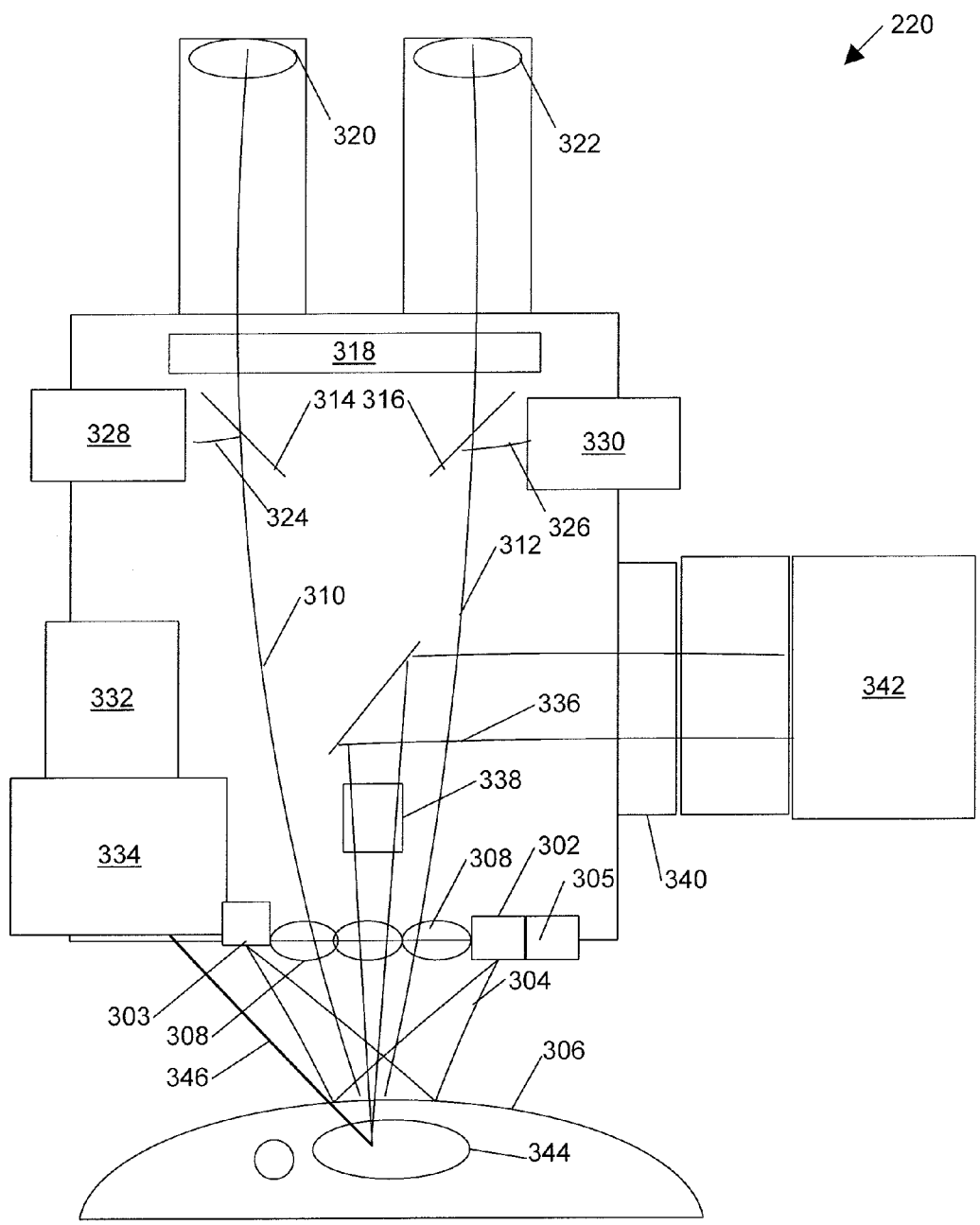
FIG. 3 illustrates an optical path for the surgical microscope of FIG. 2.

An embodiment of the fluorescent tomographic surgical microscope 220 has optical paths as illustrated in FIG. 3. This microscope has at least one white-light emitter 302 for transmitting white illuminating light 304 to a tissue surface 306, which may include portions of surface of tumor 202 and adjacent organ 204. The white light emitter 302 may be light-emitting diodes (LED's) or may be a subsystem incorporating other light sources such as halogen incandescent lamps and may incorporate lenses, and fiber optics for focusing, collecting and transmitting light for illuminating the tissue surface 306. The white light 304 may be transmitted to surface 306 through imaging lens system 308 in the manner of metallurgical microscopes, or may be transmitted to surface 306 separately in the manner of dissecting microscopes; typically, white light 304 is broad enough to evenly illuminate the entire field of view. Single or multiple white light emitters 302 are used in alternative embodiments.

As an alternative for use in fluorescence microscopy without depth resolution, white light emitter 302 may be dimmed or turned off, and blue or ultraviolet monochromatic light emitters 303 are used to illuminate the field of view. In an embodiment, blue or ultraviolet monochromatic emitters 303 have peak emission between three hundred fifty and four hundred five nanometers to induce visible fluorescence from protoporphyrin IX in tumor. Alternative embodiments may replace blue or ultraviolet flood emitters 303 with, or provide an additional set of monochromatic flood emitters 305, for providing stimulus specifically appropriate to a fluorophore other than protoporphyrin IX present in tumor. For example, near-infrared monochromatic emitters 305 may be used with other dyes such as those based on indocyanine green. In an embodiment monochromatic emitters 303, and 305 are LEDs; LEDs are available in a wide variety of spectral characteristics, can provide intense light, and are small and easy to use. In an alternative embodiment, monochromatic emitters 303 are a tungsten halogen or high intensity discharge light source equipped with a monochromatic filter for transmitting a wavelength appropriate for inducing fluorescence in fluorophores of, or metabolically produced from, the dye 208 in use. Such an alternative light source may also include optical fibers and lenses for directing light from the monochromatic filter to the tissue and tumor.

In a direct observation mode, light reflected and scattered from tissue surface 306 is collected by imaging lens system 308 as a left 310 and right 312 stereoscopic lights. Stereoscopic light 310, 312 passes through left 314 and right 316 beam-splitters and is imaged by left 320 and right 322 eyepieces as known in the art of stereoscopic microscopes. A blocking filter 318, such as a blue and ultraviolet blocking filter, for blocking light from the monochromatic emitters 303, 305 is arranged so it may be inserted into the path of stereoscopic light 310, 312 to enhance visibility of fluorescence or may be removed from the path to provide good visibility in white light. A portion 324 of the left 310, and a portion 326 of the right 312, stereoscopic lights are diverted by the left 314 and right 316 beam-splitters into a left 328 and right 330 CCD color imagers.

In an embodiment, blocking filter 318 has several filter elements, one filter element being clear and each additional filter element being a blocking filter selected for use with a particular monochromatic emitter of emitters 303, 305; together with a lever for placing a filter element of the filter elements in the optical pathway. In some embodiments, monochromatic emitters 303, 305 include a polarizing filter, and blocking filter 318 incorporates a polarizing filter oriented to block light of the same polarity as light emitted by emitters 303, 305.

A laser, such as a laser diode 332, having a wavelength suitable for exciting fluorescence in fluorophores of, or metabolically produced from, the dye 208 in use provides a beam typically of less than two millimeters width. In a particular embodiment, laser diode 332 has a wavelength of about six hundred thirty five nanometer to provide a beam of less than two millimeters width for use with protoporphyrin IX fluorophores produced in tumor from metabolism of 5-ALA. For maximum penetration into tissue, it is preferable that the wavelength be at least about six hundred nanometers and shorter than about 1000 nanometers. In other embodiments, laser diode 332 provides a wavelength suitable for use with indocyanine green. In other embodiments, laser diode 332 provides yet another wavelength suitable for use with a third dye. The beam from laser diode 332 is scanned by an x-y galvanometer mirror scanner 334 onto surface 306 of the organ, because of the scanning of the beam the area of the organ illuminated by the beam is considerably greater than the beam width. White and blue light at four hundred nanometers does not penetrate significantly into the tissue of organ and tumor, in some cases only half a millimeter or less into the surface 306 of the organ. On the other hand, the beam at six hundred thirty five nanometers penetrates to a much greater depth of more than a centimeter into the organ due to reduced absorption of light by organ and tissue at long wavelengths. Other long wavelengths such as those in the near infrared part of the electromagnetic spectrum also penetrate better than blue and white light. In an alternative embodiment, scanner 334 has a rotating mirror for scanning in one axis and a piezoelectric mirror-scanning device for scanning in another axis. In an alternative embodiment, laser diode 332 produces a fan beam having a breadth of several centimeters and width less than two millimeters, with this embodiment scanner 334 need only scan in one dimension to illuminate the entire area of the organ of interest.

While laser 332 may be a laser diode as heretofore discussed, in alternative embodiments lasers of different types, such as tunable titanium-sapphire lasers, may be used, together with such optical fibers and lenses as may be necessary to direct light from the laser to scanner 334.

Scattered, reflected, and fluorescent light 336 from organ 306 and tumor 304 passes through a lens of lenses 308, a collimating optic 338, a filter system 340, and into a high resolution CCD camera 342. Filter system 340 has a first mode for passing light of the wavelength emitted by laser 332, and a second mode for passing fluorescent-emitted light of wavelength typically ten or more nanometers longer than that emitted by laser 332 while blocking light of the wavelength emitted by laser 332.

In an embodiment where the wavelength emitted by laser 332 is about six hundred thirty five nanometers, the second mode for passing fluorescent-emitted light of filter 340 passes light of six hundred fifty nanometers and longer wavelengths. Filter 340 may also incorporate attenuators and polarizers for optimizing image quality and for avoiding overload of high-resolution CCD camera 342. In an embodiment, laser 332 incorporates a polarizer oriented at right angles to a polarizer of the filter 340 to eliminate glare from a surface reflected component of the light.

In one embodiment of the invention we are using a telecentric lens on light path 346. This lens makes sure that all light beams passing through it are parallel to one another at tissue 306 and tumor 304, thereby simplifying the computer models used for simulating the arrival of light at, the emission of light from, and diffusion of light within the organ and tumor. In a variation of this embodiment, a telecentric lens is in the path from scanner 334 to organ 306 and tumor 344. In another variation of this embodiment, a telecentric lens is in the path 336 from organ 306 and tumor 344 to filter 340 and camera 342. In another variation of this embodiment, telecentric lenses are used in both incident and received light paths. This lens makes sure that all light beams passing through it to or from the surface are parallel to one another. This telecentric lens helps ensure accurate modeling of light scattering in the tissue by ensuring only approximately parallel rays are imaged. In an embodiment, the telecentric lens is usable in both flood and tomographic modes.

In operation, the operating microscope 220 has a first mode where white light illuminator 302 is used. In this mode, a surgeon may view the organ 306 through eyepieces 320, 322, and a stereo pair of color images of the organ 306 may be captured by color CCD cameras 328, 330.

The operating microscope has a second mode for use in surface fluorescent imaging of organ 306. In this mode, white light illuminator 302 is dimmed or turned off, and blue monochromatic illuminator 303 or alternate monochromatic illuminator 305 is used. In this mode, a surgeon may view the organ 306 through eyepieces 320, 322, and a stereo pair of color images of the organ 306 may be captured by color CCD cameras 328, 330 in visible or near-infrared light. The surgeon may engage blocking filter 318 to enhance contrast. In this mode, remaining tumor 344 at the surface of organ 306 or at the surface of a surgical cavity in organ 306 may be seen by the surgeon directly through eyepieces 320, 322 or in contrast-enhanced images of extended spectral breadth on display device 234.

When used with blue or green light, this second mode provides visibility of fluorescent-labeled tumor at the surface of organ 204 or tumor 202.

In an alternative embodiment, the monochromatic illuminator provides red or near infrared light between 600 and 1000 nanometers wavelength, this light is capable of deeper penetration into organ and tumor than blue or green light. In this mode, an appropriate filter 340 (FIG. 3) and camera 342 or integral color filters of cameras 328, 330 can provide fluorescence information coming from deeper depths in the organ 306 or tumor 344 on display device 234. This provides the surgeon with non-depth-resolved information pertaining to the fluorophore distribution beneath the surface, this information may, however, be somewhat hazy due to scattering in the tissue. In an embodiment, multiple monochromatic illuminators are provided, and multiple filters 318, 340 are provided, permitting rapid selection of surface and deep imaging wavelengths, and selection of wavelengths appropriate for use with different fluorophores such as Fluorscein, protoporphyrin IX, and Indocyanine Green.

Figure 5:
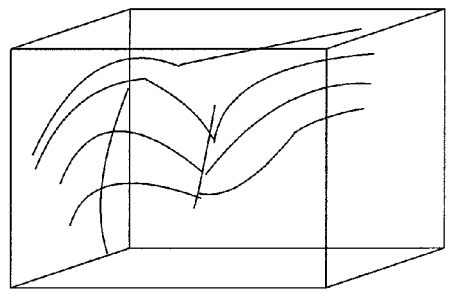
FIG. 5 illustrates a surface of the organ as reconstructed from stereoscopic images.

The operating microscope has a third, fluorescent tomographic, mode of operation. A continuous-wave embodiment of this mode, as illustrated in FIG. 4, with reference to FIG. 3, begins shortly after the surgeon washes the incision with saline to remove excess blood and other obstructions. It begins with white light illuminator 302 in use. A stereo pair of color images of the organ 306 is obtained by color CCD cameras 328, 330 and transmitted to processor 232. The white light illuminator 302 is then turned off while processor 232 traces surface features, such as vasculature, along the surface of organ 306 or an operative cavity in organ 306 as seen in both of the stereo pair of images 306. These features are compared by tracing the physical surface in three dimensions using projections into each image of the stereo pair in processor 232, and a computer model, as illustrated in FIG. 5, is computed of curvature of the surface.

The laser 332 is turned on, and its beam 346 is scanned 408 by x-y scanner 334 across the surface of organ 306, typically in a raster pattern. In an embodiment, the beam 346 of width less than two millimeters is raster-scanned across an area of approximately three centimeters by three centimeters. Within a short propagation distance, typically less than 1 mm, the photons composing the beam are completely randomized in direction because of the high scattering inherent to biological tissue. The beam 346 spreads diffusely within organ 306 because of scattering within organ 306.

Figure 6:
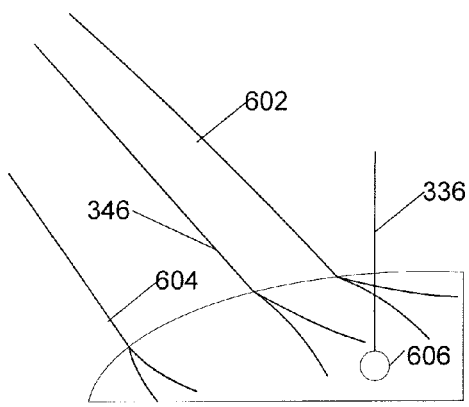
FIG. 6 illustrates a computer model of laser light propagation in the organ.

As the beam 346 is scanned, propagation of the beam through the curvature of the surface of, and into, the organ is modeled 410 by processor 232 as illustrated in FIG. 6. The modeling of beam propagation uses the three-dimensional model of curvature of the surface prepared as previously discussed with reference to FIG. 5. Details of methods of modeling light propagation in tissue have been reported by F. Leblond, S. Fortier and M. P. Friedlander, *Diffuse optical fluorescence tomography using data acquired in transmission*, in Multimodal Biomedical Imaging II, vol. 6431. Proceedings of the International Society of Optical Imaging (2007), and Davis, S. C., et al., *Contrast-Detail Analysis Characterizes Diffuse Optical Fluorescence Tomography Image Reconstruction*. Journal of Biomedical Optics, 2005. 10(5): p. 050501-1-3:

While the beam is being scanned the beam 346 stimulates fluorescence in tumor 344, which emits light 336 of longer wavelength than the light of the beam 346. The emitted light is imaged in a sequence of images by high-sensitivity charge-coupled-device (CCD) camera 342. In an embodiment camera 342 is a 16-bit thermoelectrically cooled high-sensitivity camera. The camera captures fluorescence image data.

In an alternative embodiment, filter 340 and camera 342 are replaced with a beamsplitter 370 (FIG. 3A), two filters 372, 374, and two cameras 376, 378. Light 336 is split into a first beam 380 that passes through the first filter 372, having spectral characteristics as of filter 340 in the first mode where light of the wavelength of the laser is passed by the filter, and on to a first camera 376. A second beam split from light 336 passes through the second filer 374, having characteristics as of filter 340 in the second mode where light of the wavelength of the laser is blocked, but light from fluorescence is passed, to a second camera 378. Each camera 376, 378 captures an image. In yet another alternative embodiment without beamsplitter, camera 342 has a CCD imaging device having a filter on its surface in a manner resembling the color filters of common color CCD cameras, the filter having a checkerboard pattern of from two to four types of filter elements located directly over sensor elements of the imaging device, where at least one type of the filter elements blocks light of the wavelength of the laser and passes light from fluorescence. In yet another alternative embodiment without a beamsplitter, camera 342 has an electromechanical device for exchanging filter 340 in the light path with a neutral-density filter. Images are obtained through filter 340 of fluorescent light, and through the neutral-density filter of incident light.

Figure 9:
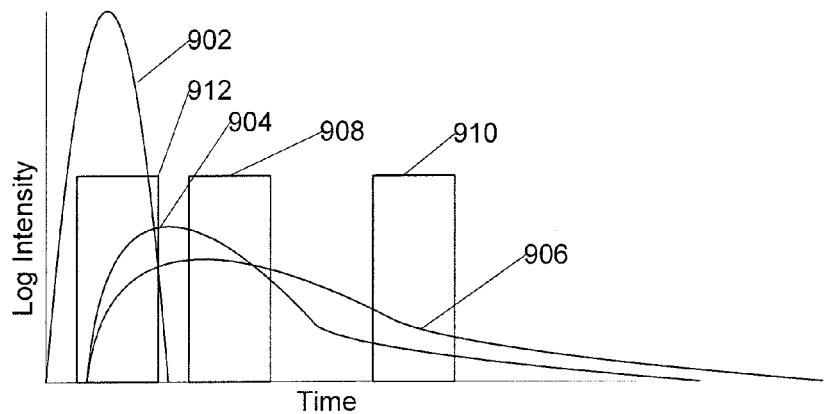
FIG. 9 illustrates fluorescence and capture windows in a time resolved embodiment of the fluorescence microscope.

In an alternative, time-domain, time-resolved, embodiment, laser beam 346 is pulsed, and high sensitivity CCD camera 342 is an intensified CCD (ICCD) camera capable of imaging fluorescence at particular time intervals following each pulse 902 (FIG. 9) of laser beam 346. This works because fluorescent light received from the organ and tumor is delayed by a random time having an exponential decay. This delay occurs for two reasons, first because incident photons enroute to the fluorophores, and fluorescent photons from the fluorophores, propagate along random courses and are scattered by numerous collisions within organ and tumor. Second, a component of this delay results because each photon emitted from fluorescent molecules such as protoporphyrin IX is typically emitted after a randomly distributed delay, or fluorescence lifetime, after absorption of an excitation photon, these delays have a distribution that decays exponentially with time as indicated in FIG. 9. The fluorescence lifetime depends in part on a local environment of the fluorophore within each cell of the tumor or surrounding tissue. As illustrated in FIG. 9, photons emitted by fluorescent molecules in normal tissues may have a different fluorescence lifetime than photons emitted by fluorescent molecules in tumor tissues.

In a particular embodiment, the laser beam 346 is pulsed at a frequency in the megahertz range. Following each pulse, the ICCD camera is enabled at a particular time relative to the pulse, and then disabled, thereby capturing photons received in a particular capture time window, such as window 908. By comparing images obtained with an early 908 and a late 910 capture time window, a time distribution of received and detected fluorescent photons is determined. From this time distribution of received and detected fluorescence photons, a fluorescence lifetime of fluorescence of fluorophores in the tissue is determined in a time-resolved version of the system. It is expected that, because of absorption, scattering, and re-emission, fluorophores in deeper tumors will appear to have later peak emission with a longer tail, such as relaxation time curve 906, than fluorophores in shallower tumors that following a faster relaxation curve 904. In this time-resolved system, a false-color image of fluorescence lifetime and intensity is displayed to the surgeon to help indicate locations of tumor tissue to the surgeon. In one embodiment, the signal associated with the later time-bins is used to produce planar images and may also be used as signal input for tomographic computations. The information conveyed by late time bins is related to deeply buried tumors because those detected photons are those associated with fluorescence molecular events for which the light paths are the longest.

In the time-resolved system, a series of calibration pulses may be used to collect a time histogram of the pulsed-laser's excitation pulses. The ICCD camera of the time-resolved system is also more sensitive to small concentrations of fluorophores than other embodiments having CCD cameras without integral intensification.

In another embodiment, time-resolved signals are acquired using photomultiplier tubes coupled to single photon counting technology instead of an ICCD camera.

In a time-resolved embodiment, the beam 346 is scanned across the surface and tumor twice, first with filter 340 configured to pass light from laser 332 and camera 342 configured to capture light in an illumination window 912 during each pulse of the beam 346 to provide a stimulus-wavelength image. The beam 346 is scanned with filter 340 configured to block light from laser 332 while passing the longer-wave fluorescent light with camera 342 alternately configured to capture fluorescence-emission images during a first fluorescence capture window 908 and in a delayed fluorescence capture window 910. A sequence of image pairs with laser light blocked by filter 340 in first and delayed capture windows, and a sequence of images with laser light passed by filter 340, are passed by camera 342 to processor 232 for processing.

In an alternative embodiment, known as a frequency domain embodiment, laser illuminator 332 is modulated at a high frequency, in a particular embodiment laser 332 is amplitude modulated at approximately one hundred megahertz. Since light scattered by tissue, and fluorescent light, is delayed relative to light emitted by the laser, and somewhat spread out in time, each pixel sensor of camera 342 therefore receives scattered and fluorescent light that is amplitude modulated at the same frequency as, but with a phase shift with respect to, the light emitted by illuminator 332.

In this frequency domain embodiment, camera 342 has a rectilinear array of pixel sensors organized in rows and columns. In this embodiment, each pixel sensor of a selected row of pixel sensors is coupled to circuitry for measuring the phase shift between the modulation of laser 332 and the modulation of light received by that pixel. Rows are coupled to the circuitry for measuring phase shift in succession for each frame of an image; an image recorded by camera 342 therefore is an array of phase shifts. Camera 342 is also adapted to recording an image that is an array of intensity, as in conventional digital cameras.

Figure 10:
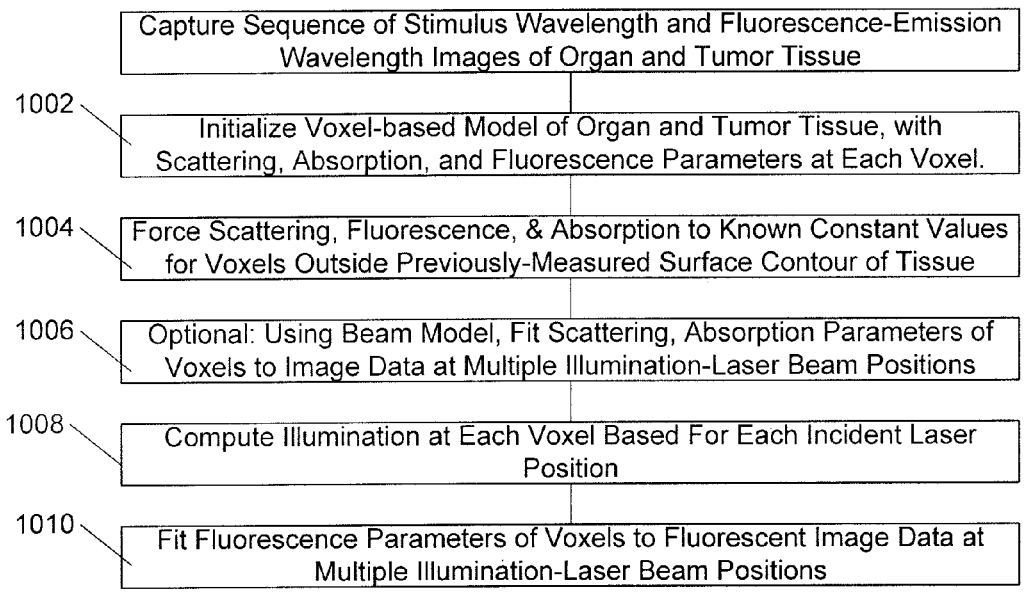
FIG. 10 is a flow chart of the method of determining voxel fluorophore concentrations.

The image array of phase shifts and the image of intensity captured by camera 342 are used with a model of the organ surface in algorithms similar to those previously discussed with reference to FIGS. 4 and 10 to refine parameters of a model of light propagation in a three dimensional model of the organ 306 and lesion or tumor 344.

In some applications of the microscope other than open brain surgery, there may also be a matching liquid applied to the subject to give the area being interrogated a geometry that is simpler to model.

The tomography reconstruction algorithm is based on the assumption that the received light from the tissue is diffused, resulting from scattering and absorption at each voxel in a model of the tissue. Each voxel is assigned a scattering parameter, an absorption parameter, and fluorescence parameters, such as concentration and fluorophore lifetime 1002. It should be noted that the fluorophore lifetime parameter can be refined and displayed as an image only with the time-resolved and frequency-domain embodiments; while the fluorophore concentration parameter can be refined and displayed in time-resolved, frequency-domain, and continuous-wave embodiments.

Voxels external to the modeled surface contour of the tissue have absorption, scattering, and fluorescence parameters assumed to be constant, known, and zero in most cases 1004 to set boundary conditions on the model of the tissue during the process of solving the differential equations associated with light transport. Voxels within the organ, tumor, or tissue are initially assumed to scatter light and have absorbance as per an average absorption and scattering of biological tissues of the tissue type being observed. In some applications the average values of these properties are chosen based on literature values.

In an alternative embodiment, using modeled refraction and incident angle of the laser beam 346 at initially illuminated voxels, and modeled diffusion of beam, a least-squares fit is performed using measured stimulus-wavelength image data to refine 1006 the absorption and scattering parameters at each voxel. In this process, stimulus-wavelength image data is used from multiple positions of the incident beam 346. In this embodiment, optical diffuse tomography images of absorbance may be displayed to the surgeon, showing concentrations of chromophores in the tissue. These images may be of use during surgery in locating hidden structures such as blood vessels, aneurysms, and other concentrations of heme.

Once the absorption and scattering parameters are refined, or in embodiments displaying fluorescent parameters only a default absorption and scattering parameters may be used; for voxels within the tissue an illumination at each voxel is computed 1008 for each position of the incident beam 346 using a computer-based light propagation model of the tissue and organ.

Next, the fluorescence concentration parameters of each voxel are computed 1010 by using a least-squares fit of the fluorescence parameters to the captured fluorescence image data for multiple positions of the scanned incident laser beam 346. The fluorescence parameters thus computed for each voxel form a three-dimensional model of fluorophore distribution in the tissue.

Figure 7:
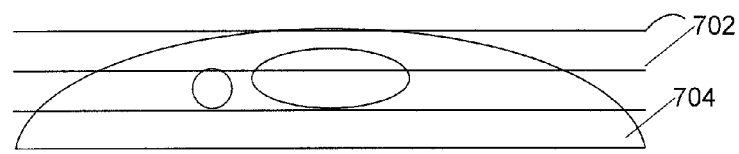
FIG. 7 illustrates a three-dimensional computer model of fluorescence in the organ and tumor, with tomographic slices.

A sequence of tomographic images is constructed and displayed 414 by considering intersections of a plane with fluorescence distribution of the three-dimensional model of fluorescence distribution of planes 702 intersecting the model 704 of fluorophore distribution as illustrated in FIG. 7. In an embodiment, these tomographic images are displayed on display device 234 to the surgeon as a sequence of increasing depth, the sequence being preceded by a white light photographic image of the organ or cavity for reference.

In an embodiment wherein refinement of the absorbance and scattering parameters of each voxel need not be done, the fluorescence signal is normalized by ratioing received fluorescence signals to brightness of the stimulus-wavelength image in order to partially compensate for absorbance and scattering in tissue. This data normalization scheme also partially compensates for the lack of precise focus of the fluorescent images captured by the camera 342. The normalized images form a data vector, b. Then the matrix inverse problem b=A x, where A is the model and x the fluorescence image, is solved.

Figure 8:
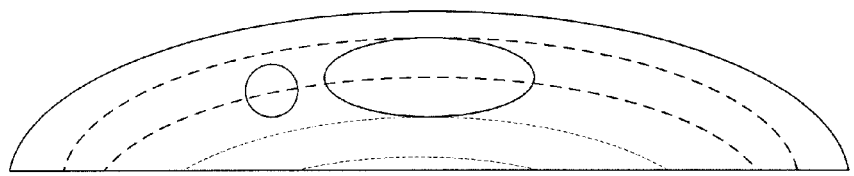
FIG. 8 illustrates a three-dimensional computer model of fluorescence in the organ and tumor, with false-color projections of fluorophore concentration at depth provided to show the surgeon location and depth of tumor portions.

In an alternative embodiment, as illustrated in FIG. 8, a sequence of surfaces of increasing depth into tumor and organ 306 is computed from the computer model of the surface, each of these curved surfaces corresponds to the organ surface or a specific distance below the curved organ surface. A sequence of tomographic images is computed by determining florescence distribution in voxels along each of these surfaces. In an embodiment, these tomographic images are displayed on display device 234 to the surgeon as a sequence of increasing depth, the sequence being preceded by a white light photographic image of the organ or cavity for reference. In an alternative embodiment, the tomographic images of increasing depth are encoded by coloring each image with a false color ranging from blue for images at the organ surface to red for images more than a centimeter deep into the surface. These images are then summed. The sum image, having fluorescence intensity encoded as intensity and fluorescence depth encoded as color, is then displayed on display device 234. White light images and images of reflected and scattered laser light may also be displayed on display device 234 to provide the surgeon with a visual reference.

Once the laser scanning 408 is complete, and while image processing proceeds, white light illuminator 302 is turned back on. Once the surgeon studies the tomographic images on display device 234, the surgeon may remove additional tumor or other organ tissue and repeat the process illustrated in FIG. 4.

In an embodiment, computer simulation of the microscope 220 shows that fluorescence of protoporphyrin IX generated by 5-ALA tagging of tumor tissue can be resolved to about two and a half millimeter resolution to a depth of twelve millimeters in organ 306. Further, presence of strong concentrations of protoporphyrin IX can be detected to a greater depth than that at which this resolution can be obtained.

Studies of a mouse model of glioma show that removal of protoporphyrin-IX-tagged tumor tissue detected at the surface of an operative site with a surface fluorescence microscope enhance survival; this has also been shown to be true by Stummer for human glioma. It is expected that microscope 220 will result in both improvements in survival beyond those obtained with surface fluorescent instruments and a reduction in post-surgical neurological impairment.

It is also expected that the microscope 220 will be of use in treating other cranial tumors such as meningioma, pituitary tumors, acoustic neuroma, and some metastatic tumors. It is expected that the microscope 220 will also be of use in surgical treatment of tumors in other sites, including skin, breast, liver, bowel, thyroid, eyes, pancreas, kidney, bladder, prostate and muscle, as well as some lesions of other types including vascular abnormalities.

The microscope 220 is also of use with indocyanine green for visualization of aneurismal vasculature obscured by overlying vessels, aneurysms, or other tissue.

Figure 12:
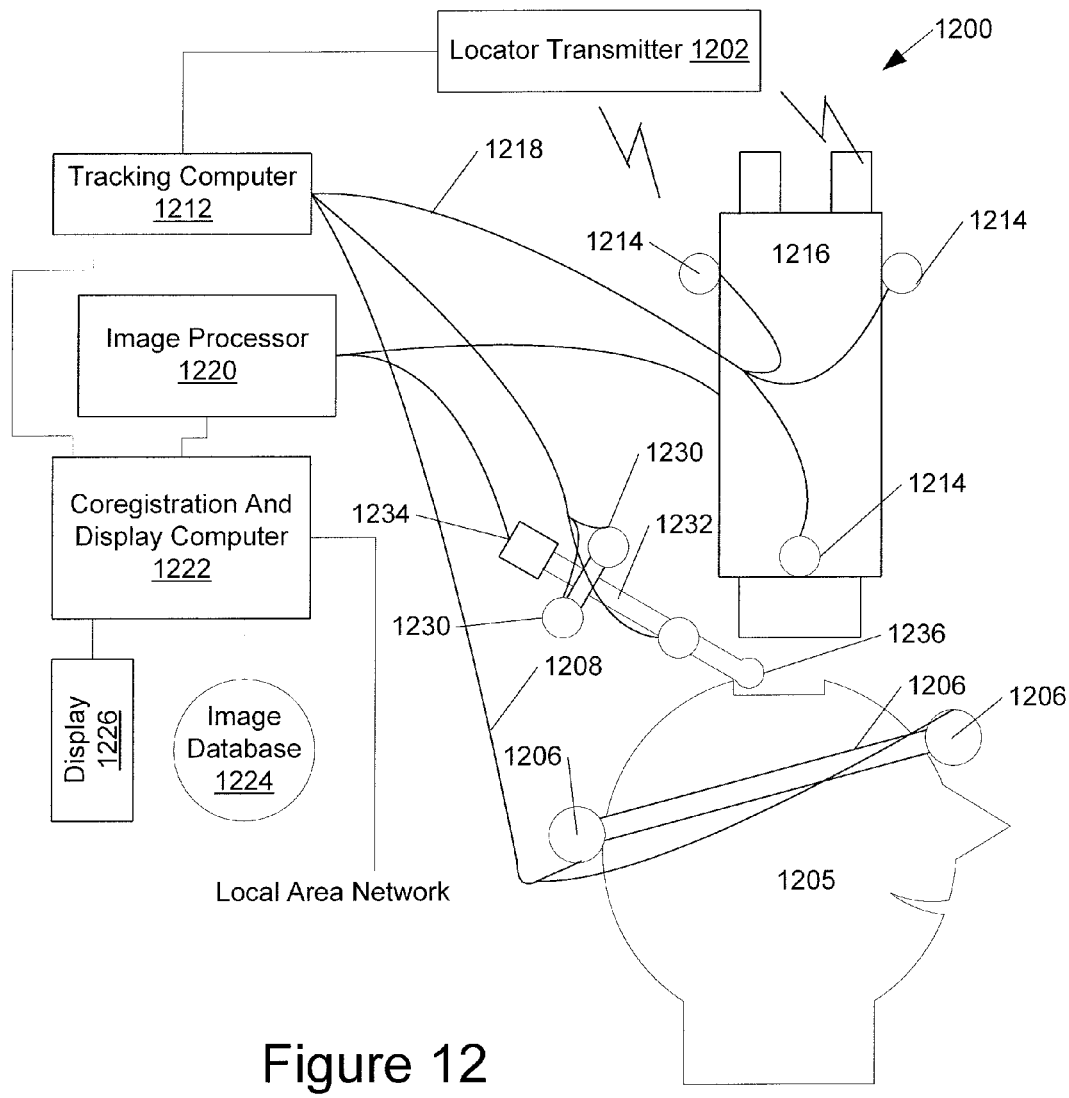
FIG. 12 illustrates an embodiment where tracking devices track location of patient and fluorescent tomographic microscope, permitting image registration.

In the coregistration embodiment 1200 of FIG. 12, a locator transmitter 1202 is provided in an operating room, preferably transmitter 1202 is placed at a location that will remain constant throughout an operation such as on a wall, an operating table, or some other object that will not often move unexpectedly during an operation. A head-locator frame 1204 is attached to the head of a subject 1205, and at least three subject locator sensors 1206 are attached to the head locator frame 1204. The locator transmitter 1202 transmits a signal to the subject locator sensors 1206. A cable 1208 connects subject locator sensors 1206 to a tracking computer 1212.

Similarly, additional, or microscope, tracking sensors 1214 are attached to a fluorescent tomographic operating microscope 1216 as previously described with reference to FIG. 3. Operating microscope 1216 operates in conjunction with image processor 1220 that performs the fluorescent tomographic imaging reconstruction as previously described; this reconstruction is performed in a set of fluorescent tomographic coordinates F. A cable connects these additional sensors 1214 to the tracking computer 1212. Again, at least three non-collinear sensors 1214 are provided.

Tracking computer 1212 uses signals from the locator sensors 1206 to track the patient locator sensors 1206 and microscope locator sensors 1214 to determine a three-dimensional location of each locator sensor 1206, 1214. The locator sensors are tracked in a three dimensional coordinate system relative to the locator transmitter 1202 and herein referred to as room coordinates W.

Other embodiments may embody other apparatus for tracking location of the microscope; such other apparatus may include mechanical linkages and optical tracking devices.

Coregistration and display computer 1222 must determine a mapping between the room coordinates W and the fluorescent tomographic coordinates F. To do so, coregistration and display computer 1222 inputs locations of all three microscope sensors 1214 in room coordinate W terms from tracking computer 1212, determines a transformation based on a location and orientation of microscope 1216, and executes the transformation.

The coregistration and display computer 1222 also inputs locations of all three subject locator sensors 1206, and computes a transformation between subject coordinates S and room coordinates W. Coregistration and display computer 1222 has access to a database 1224 containing preoperative imagery such as may have been obtained by magnetic resonance imaging (MRI) or computed x-ray tomography (CT) techniques as known in the art of medicine. These images may be in subject coordinates, or in yet another coordinate system C. Coregistration and display computer 1222 executes transformations to convert the fluorescent tomographic imagery in from fluorescent tomographic coordinates into subject S or other coordinates C, and then superimposes these tomographic images on the preoperative imagery as viewed on display 1226 so that a surgeon can correlate tissue and organ seen through microscope 1216 to preoperative imagery and make decisions relevant to surgical procedure.

In an alternative embodiment, additional wand tracking sensors 1230 are attached to a wand 1232. Wand 1232 has a laser illuminator 1234 and scanning mirrors 1236. In this embodiment locator transmitter 1202 and tracking computer 1212 track locations of wand tracking sensors 1230 in room coordinates W, and derives a wand angle and scanning mirror 1236 location therefrom. This wand angle and scanning mirror location are translated into fluorescent tomographic coordinates F and passed to image processor 1220.

In an additional operating mode of this embodiment, and with reference to FIG. 3 as well as FIG. 12, wand laser illuminator 1234 and scanning mirrors 1236 are used instead of microscope laser illuminator 332 and scanning mirrors 334 while performing the method of FIG. 4.

The alternative embodiment with wand may offer advantage by allowing operation with incident beam 346 angles not possible with the embodiment of FIG. 3. In particular, it may be possible to place the wand behind portions of tissue so as to visualize fluorescent tumor tissues 344 located deeper in the organ 306 than otherwise, or to illuminate tumor tissue 344 from angles that allow better visualization.

In an alternative embodiment of the coregistering embodiment discussed with reference to FIG. 12, the microscope operates in non-depth-resolved surface fluorescence mode, and it is these images that are coregistered to the preoperative MRI data.

Light as the term used herein includes electromagnetic of the visible, near ultraviolet and near infrared portions of the spectrum that may be focused with lenses and imaged with readily available semiconductor imaging devices.

While the invention has been described with reference to fluorescent substances such as indocyanine green, protoporphyrin IX, and Fluorescein, the apparatus and methods herein described are applicable to other biocompatible fluorescent prodrugs, dyes and molecules such as are known or may be developed in the future, and which may tend to concentrate in tumor tissue to a different extent than in normal tissue.

An alternative embodiment of the method uses the fluorescent tomographic microscope heretofore described to visualize a fluorescent chromophore such as may occur naturally in some types of tumor tissues. In this embodiment, there is no need to administering a prodrug or a drug. The fluorescent tomographic microscope may also be used to visualize tumors or tissues having concentrations of such a naturally occurring fluorescent chromophore that differ from concentrations in nearby normal organ stroma. Nicotinamide Adenine Dinucleotide Hydride (NADH) is an example of a naturally-occurring fluorescent chromophore that is critical to function of mitochondria. As such NADH occurs in all eukaryotic tissues, including human organ stroma and tumor tissues, but may be present at different concentrations in tumor and nearby normal stroma. Metabolically inactive tissues, such as fatty tissue of breast, may have very low concentrations of NADH, while adjacent malignant tumor tissue may be metabolically very active and therefore possess large quantities of NADH; this difference in concentration permits using the fluorescent tomographic microscope to visualize the malignant tumor tissue.

In an alternative embodiment, which may but need not utilize a fluorescent chromophore, the absorbance and scattering parameters at the wavelength of the laser are refined for each voxel as heretofore described. This absorbance and scattering parameters are mapped onto a plurality of planes intersecting the model of the tissue, and displayed as a tomographic image.

Figure 13:
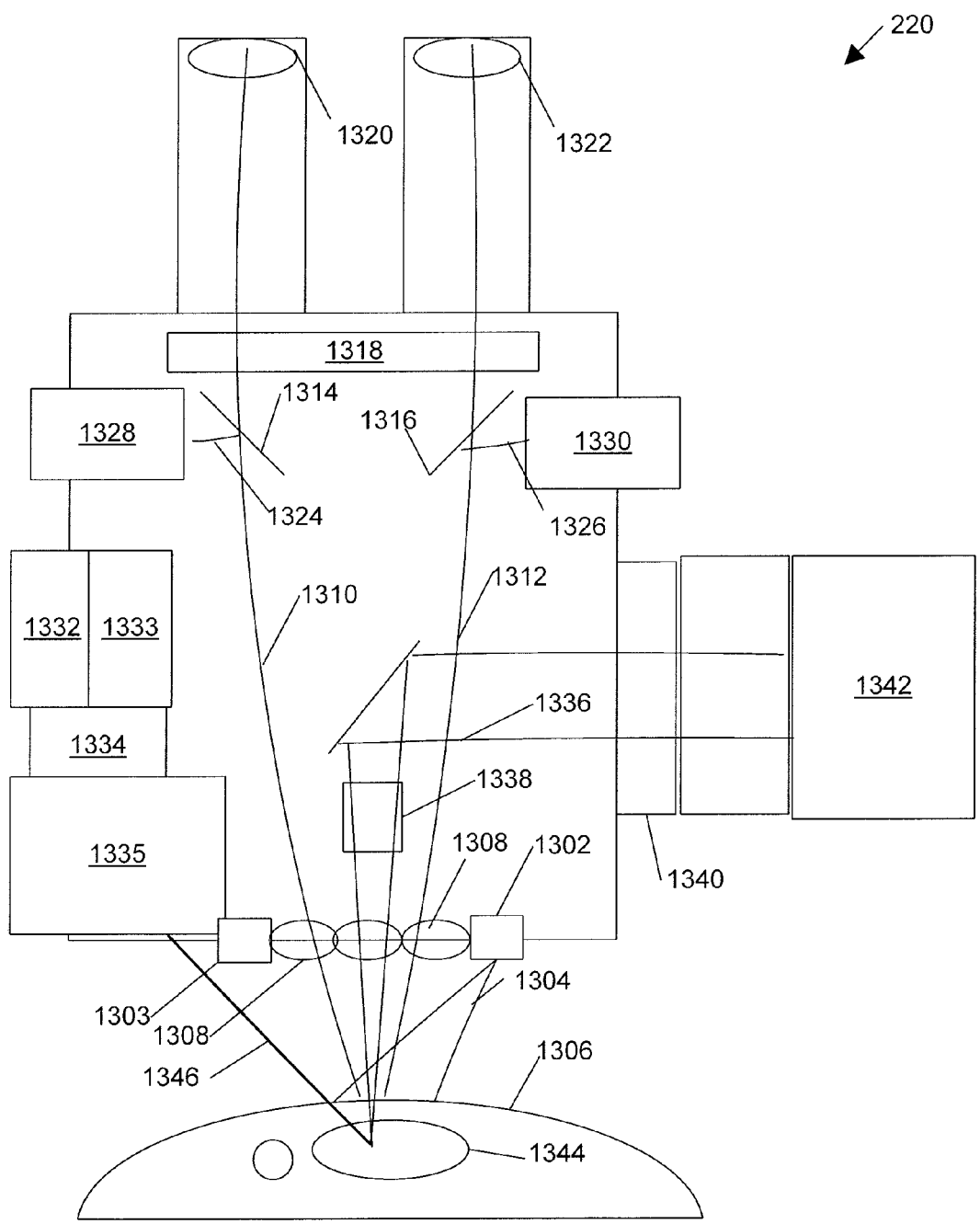
FIG. 13 illustrates an alternative embodiment capable of tomographically resolving absorbance at multiple wavelengths, and of producing tomographic images of absorbance and of producing images of heme oxygenation in addition to fluorescence images.

An alternative embodiment of the fluorescent tomographic surgical microscope 220 has optical paths as illustrated in FIG. 13. This microscope has at least one white-light emitter 1302 for transmitting white illuminating light 1304 to a tissue surface 1306, which may include portions of surface of tumor 202 and adjacent organ 204. The white light emitter 1302 may be light-emitting diodes (LED's) or may be a subsystem incorporating other light sources such as halogen incandescent lamps and may incorporate lenses, and fiber optics for focusing, collecting and transmitting light for illuminating the tissue surface 1306. The white light 1304 may be transmitted to surface 1306 through imaging lens system 1308 in the manner of metallurgical microscopes, or may be transmitted to surface 1306 separately in the manner of dissecting microscopes; typically, white light 1304 is broad enough to evenly illuminate the entire field of view. Single or multiple white light emitters 1302 are used in alternative embodiments.

As an alternative for use in fluorescence microscopy without depth resolution, white light emitter 1302 may be dimmed or turned off, and blue or ultraviolet monochromatic light emitters 1303 are used to illuminate the field of view as described with reference to FIG. 3.

In a direct observation mode, light reflected and scattered from tissue surface 1306 is collected by imaging lens system 1308 as a left 1310 and right 1312 stereoscopic lights. Stereoscopic light 1310, 1312 passes through left 1314 and right 1316 beam-splitters and is imaged by left 1320 and right 1322 eyepieces as known in the art of stereoscopic microscopes. A blocking filter 1318, such as a blue and ultraviolet blocking filter, for blocking light from the monochromatic emitters 1303 is arranged so it may be inserted into the path of stereoscopic light 1310, 1312 to enhance visibility of fluorescence or may be removed from the path to provide good visibility in white light. A portion 1324 of the left 1310, and a portion 1326 of the right 1312, stereoscopic lights are diverted by the left 1314 and right 1316 beam-splitters into a left 1328 and right 1330 CCD color imagers.

A first laser, such as a laser diode 1332, operates at a first wavelength. A second laser, such as laser diode 1333, operates at a second wavelength. Beams from the first 1332 and second laser 1333 are combined by a combiner 1334 into a beam. In an embodiment, first laser 1332 and second laser 1333 are operated at separate times to allow capturing separate frames in camera 1342 of response to the first laser 1332 and of response to the second laser 1333.

For maximum penetration into tissue, it is preferable that the wavelength of first and second lasers 1332, 1333 are at least about six hundred nanometers and shorter than about 1000 nanometers. In some embodiments, laser diode 1332 provides a first wavelength suitable for use with fluorescent chromophores such as protoporphyrin IX or indocyanine green. In other embodiments, laser diode 1332 provides yet another wavelength chosen for deep tissue penetration and imaging of heme having a particular degree of oxygenation. Laser diode 1333 provides a second wavelength chosen for deep tissue penetration and use with the first wavelength to distinguish a degree of oxygenation of heme. In alternative embodiments, additional lasers 1332, 1333 are used at additional wavelengths for resolving additional chromophore types and to allow characterization of tissue-dependent scattering properties such as average local density and size of scattering particles. In an alternative embodiment, a single, but tunable, laser 1332 is used.

The beam from combiner 1334 is scanned by an x-y galvanometer scanner 1335 onto surface 1306 of the organ, because of the scanning of the beam the area of the organ illuminated by the beam is considerably greater than the instantaneous beam width. Since both wavelengths of the beam 1346 are in the red and/or infrared, they penetrates to a much greater depth than does white light, a depth of more than a centimeter into the organ due to the reduced absorption of light by organ and tissue at long wavelengths. In an alternative embodiment, scanner 1335 has a rotating mirror for scanning in one axis and a piezoelectric mirror-scanning device for scanning in another axis; other combinations of piezoelectric, galvanometer, and rotating mirrors are contemplated as permissible variations.

In this embodiment, scattered, reflected, and fluorescent light 1336 from organ 1306 and tumor 1344 passes through a lens of lenses 1308, a collimating optic 1338, a filter system 1340, and into a high resolution CCD camera 1342. Filter system 1340 has transparent modes for use with multiple wavelengths for imaging heme, as well as excitation-wavelength blocking and fluorescent-light passing modes for use when imaging fluorescent chromophores. In an embodiment, CCD camera 1342 is actively cooled to provide reduced noise and enhanced sensitivity to infrared light.

In operation, in a heme imaging mode, images are captured by CCD camera 1342 at each of the three wavelengths separately; these images are passed to the image processing system 232 for processing. Image processing at the first and third wavelengths is as heretofore described with reference to FIG. 10; however absorbance and scattering parameters are refined as indicated in step 1006. Image processing at the second wavelength is performed by constructing the voxel-based model of scattering and absorbance 1002 at the second wavelength, but without fluorescence parameter. The absorbance parameters at each voxel are then ratioed to provide a measure of heme oxygenation at each voxel, and summed to provide a measure of heme concentration at each voxel.

The fluorescence, heme concentration, and heme oxygenation parameters at each voxel are then mapped into tomographic image planes and displayed as tomographic images for inspection by the surgeon. The surgeon can then use these images to distinguish tumor from adjacent and nearby normal organ stroma. This embodiment is useful during surgery for visualizing below-surface heme concentrations as well as fluorescence during a wide variety of surgical procedures; and is of particular utility for distinguishing malignant breast tissue from adjacent normal breast tissue. In addition to cancer surgery, this embodiment is also useful for intraoperative identification of berry aneurisms, arteriovenous malformations, hematomas, and blood vessels.

An embodiment as heretofore described with reference to FIG. 13 is capable of imaging heme and heme oxygenation below organ surfaces in real time, and is capable of generating an additional tomographic image indicating changes in heme concentration and/or heme oxygenation. These images indicating changes in heme concentration and oxygenation are useful for functional neuroimaging to confirm identification of foci of seizure activity because neural activity depletes oxygen and increases blood flow. Precise identification of foci of seizure activity is of importance during surgical procedures intended to alleviate epilepsy, and such surgery is occasionally done under local anesthesia to permit identification of such foci. Since the apparatus can identify changes in heme concentration and oxygenation over a centimeter below a surface, this embodiment may also be used for functional neuroimaging through the intact skull, although resolution is less than that available with the skull open.

In an alternative embodiment resembling that of FIG. 13, additional lasers operating at additional wavelengths are used. This embodiment may provide improved resolution of heme concentrations, and may also be used to distinguish lipid and water concentrations in tissue.

In an alternative embodiment resembling that of FIG. 13, lens system 1308 has little magnification, the white light and surface fluorescence illuminators 1302, 1303, optical eyepieces 1320, 1322, and filter 1318 may but need not be omitted. This embodiment is useful for non-contact imaging through skin of human breast tissue without need of matching fluid.

Embodiments Using Depth-Dependent Absorption of Fluorescent Light

In an alternative embodiment, fluorescence excitation of fluorophores in tissue is performed using a broad-beam source in the NIR at the excitation wavelength, $\lambda_{ex}$. It has been found that fluorescent light emitted by concentrations of fluorophores like protoporphyrin IX is more strongly absorbed by tissue in the 650-670 nanometer wavelength range than in longer wavelengths such as near 700-710 nanometers, and that with proper stimulus radiation, protoporphyrin IX will emit radiation having wavelengths from 650 to 720 nanometers. Similar effects may also occur with fluorescent light emitted by other fluorophores at similar or other wavelengths. This effect is due to the presence in tissue of chromophores, substances—including hemoglobin—in tissue that absorb or scatter light more intensely at some wavelengths than others. Typically, though, while fluorescent radiation is emitted across this range, the emitted radiation is not uniform in intensity across the wavelength band.

Figure 16:
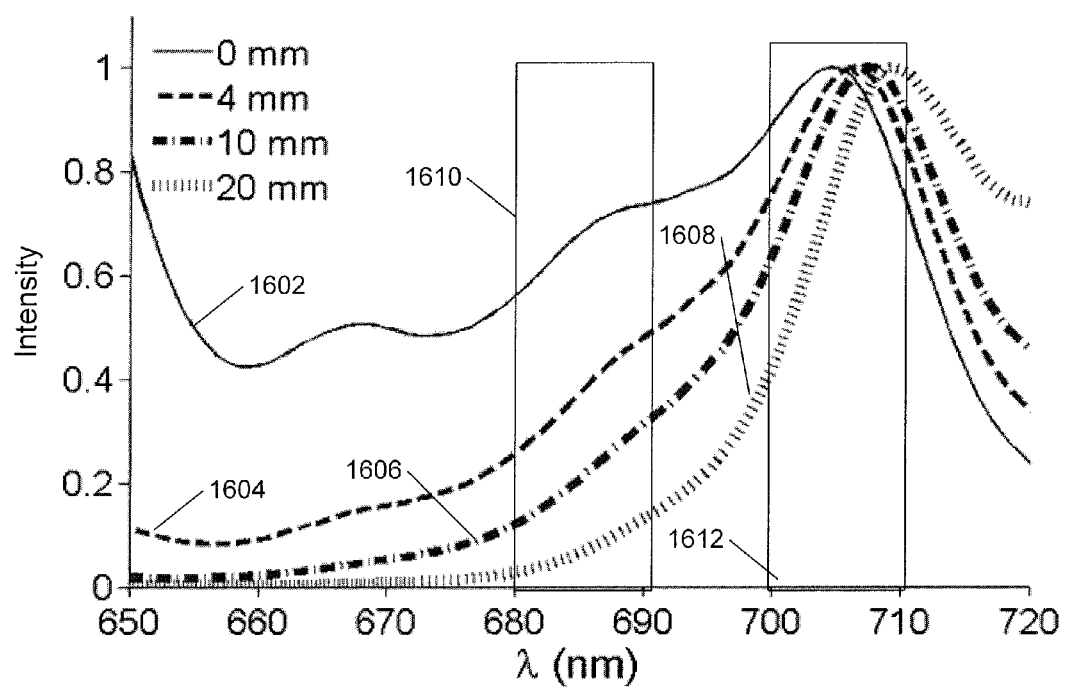
FIG. 16 illustrates spectra of fluorescent light emitted at several depths in tissue and measured above a surface of tissue.

FIG. 16 illustrates spectra of fluorescent radiation emitted by fluorophores at several depths in tissue as observed above the tissue. These spectra have been normalized to the same peak level. Spectra 1602 is that of fluorophores at the surface of the tissue, and is close to the spectra of light as emitted by the fluorophores themselves. Spectra 1604 is that of light from fluorophores four millimeters below the surface as seen from above the surface, spectra 1606 is that of light from fluorophores one centimeter below the surface as seen from above the surface, and spectra 1608 is that of light from fluorophores two centimeters below the surface as observed from above the surface.

In an embodiment for use with the prodrug 5-ALA and the fluorophore protoporphyrin-IX, emitted fluorescence signals are measured at two wavelengths, $\lambda_{1,2}$, each of which is longer than the excitation wavelength $\lambda_{ex}$, using band-pass filters and a cooled CCD camera; in other embodiments emitted fluorescence signals are measured at multiple, meaning three or more, wavelengths using appropriate band-pass filters having center pass-band wavelengths at different wavelengths in the range of 650-720 nanometers. For example, if tissue has absorption and scattering characteristics similar to the tissue assumed in FIG. 16, and fluorescent light intensity I1 is measured through a filter having bandpass 1610 between 680 and 690 nanometers while a fluorescent light intensity I2 is measured through a filter having bandpass 1612 between 700 and 710, a ratio of I1 to I2 will be considerably smaller when the fluorophore is two centimeters below the surface than when the fluorophore is at the surface of the tissue.

Figure 14:
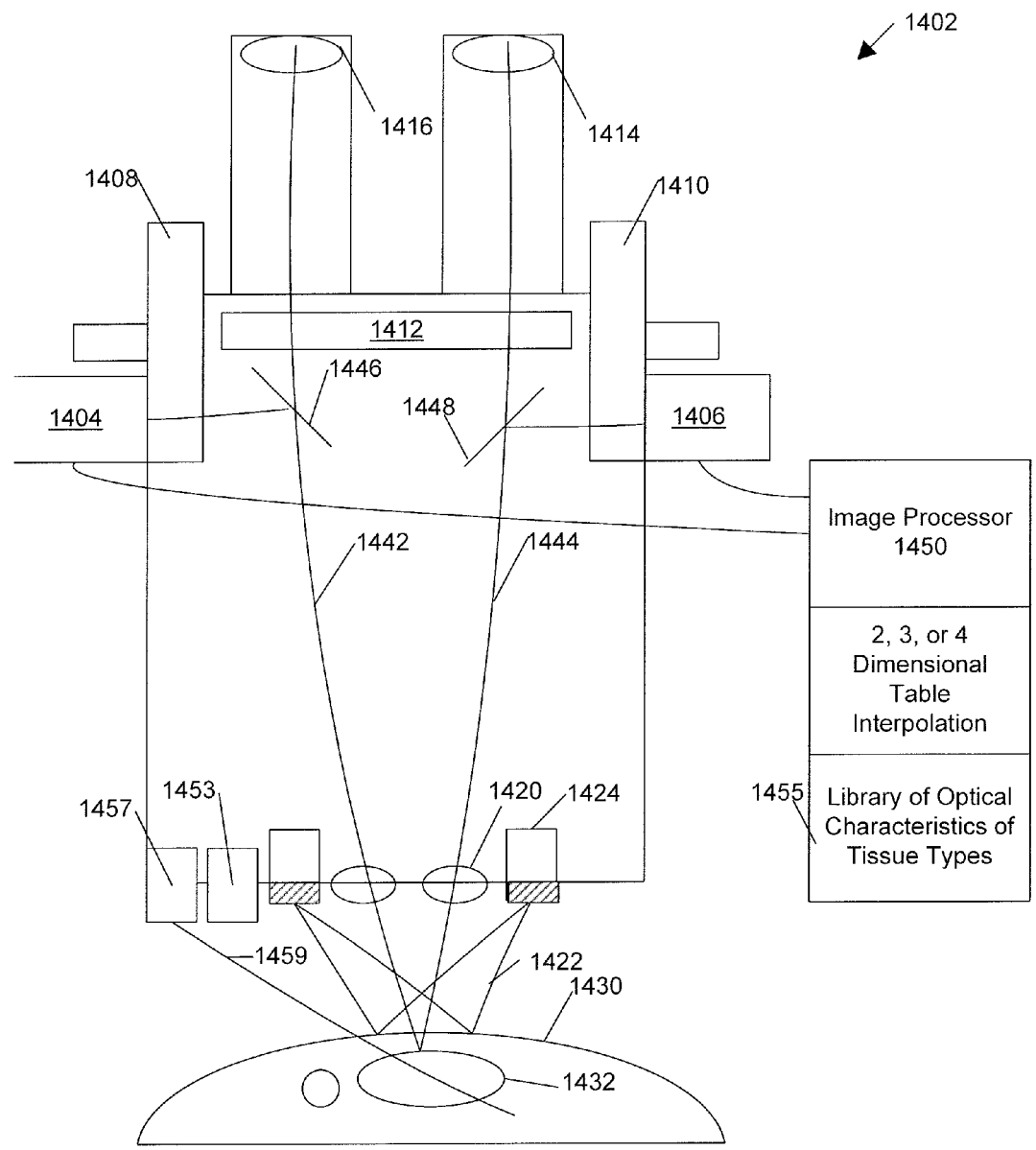
FIG. 14 illustrates an alternative embodiment capable of using spectral information to resolve depth of fluorophore concentrations in tissue.

Embodiments for use with other fluorophores than protoporphyrin IX will require different calibration tables and may operate at wavelengths other than those specified in the previous paragraph. Further, it is known that optical absorption and scattering characteristics differ from one type of tissue to another, and may also change somewhat with time as a subject's oxygenation levels change during surgery. In order to provide for this variability, an embodiment, as illustrated in FIG. 14, has a library 1455 with normal optical characteristics of a variety of tissue types that the fluorescent tomographic microscope is expected to encounter during surgery. For example, the library may contain optical characteristics for normal brain grey matter and for normal brain white matter when the microscope is used during removal of brain tumors such as gliomas. An operator then selects the appropriate tissue type for tissue in the field of view, and optical characteristics of that tissue type are then used for computation of fluorophore depth and distribution.

In an alternative embodiment, library 1455 has optical characteristics of a variety of tissue types with each tissue type measured under different levels of oxygenation. In these embodiments, the operator measures tissue oxygenation with direct or optical techniques and optical characteristics of the tissue are determined based on both tissue oxygenation and tissue type.

In alternative embodiments, optical characteristics of tissue in the field of view of the microscope are determined at the wavelengths of interest on the fly. In these embodiments, a tunable laser, such as laser 1457 (FIG. 14), projects a beam 1459 into the tissue at an angle. The laser 1457 is sequentially tuned to wavelengths in the passband of each bandpass filter of filters 1408, 1410, or filter 1528 of FIG. 15, or filter 1340 of FIG. 13. Images are obtained of scattered light from beam 1459 through each bandpass filter as beam 1459 penetrates into, and is scattered and dispersed by, the tissue 1430, 1512 Optical characteristics of the tissue under current levels of oxygenation are determined from the images of scattered light. Laser 1457 is then turned off, and these determined optical characteristics are then used for computation of fluorophore depth and distribution.

Assuming that tissue absorption due to the fluorophore concentrations of tumor is much smaller than absorption by other chromophores of tissue, the light signals at each emission wavelength can be modeled using the expression $$\psi^{em}(\vec{R},\lambda^{ex},\lambda) \approx Q_F \varepsilon_F^{em}(\lambda) \int_\Omega d^3 r \psi^{ex}(\vec{r}) C_F(\vec{r}) G^{em}(\vec{R},\vec{r},\delta^\lambda,D^\lambda) \quad \text{(Eqn. 1)}$$

where $\vec{R}$ is the vector corresponding to the detection point on the tissue surface, which is mapped onto a pixel or sub-ensemble of pixels on the CCD chip. $Q_F$ is the quantum yield, $\varepsilon_F^{em}(=)$ the emission spectrum and $C_F(\vec{r})$ the concentration of fluorescent molecules at location $\vec{r}$, where $\vec{r}$ is an arbitrary vector corresponding to the location of a point inside the interrogated tissue. In equation (1), light transport is modeled as a diffusive process. The fluence function $\psi^{ex}$ is the excitation light field, and $G^{em}$ is the diffusion equation Green's function, which corresponds to the radiant exposure in response to a light impulse at $\vec{r}$. For boundary conditions associated with an infinite homogenous medium, it is given by $$G_\infty^{em}(\vec{R},\vec{r},\delta^\lambda,D^\lambda) = \frac{\exp(-1|\vec{R}-\vec{r}|/\delta^\lambda)}{4\pi D^\lambda |\vec{R}-\vec{r}|}, \quad \text{(Eqn. 2)}$$

where the diffusion constant is $D^\lambda = \frac{1}{3}(\mu_a^\lambda + \mu_s'^\lambda)$ and the penetration depth is $\delta^\lambda = \sqrt{D^\lambda/\mu_a^\lambda}$. $\mu_a^\lambda$ is the absorption coefficient of the tissue while $\mu_s'^\lambda$ is the reduced scattering coefficient.

A closed form expression is derived from Eqn. 1 and Eqn. 2, from which a depth value can be estimated for each point imaged on the tissue surface, using an approximation that all fluorescence emitted from the surface is from a point-like distribution of fluorophore with molar concentration $C_F$ location at position $\vec{r}_s$. This is equivalent to setting $C_F(\vec{r}) = C_F \delta^{(3)}(\vec{r} - \vec{r}_s)$ in Eqn. 1, which then takes the form $$\psi^{em}(\vec{R},\lambda^{ex},\lambda) \approx C_F Q_F \varepsilon_F^{em}(\lambda) \psi^{ex}(\vec{r}_s) G^{em}(|\vec{R} - \vec{r}_s|,\delta^\lambda,D^\lambda) \quad \text{(Eqn. 3)}$$

where the depth of the distribution is $|\vec{R} - \vec{r}_s| = d$ assuming that the detection point $\vec{R}$ is located directly above the source of fluorescence at $\vec{r}_s$.

To illustrate how fluorescence spectra are affected by varying the depth of the fluorophore distribution, see FIG. 16 for protoporphyrin-IX spectra computed with Eq. (3) for depths varying up to d=20 mm for an anticipated typical absorption spectrum labeled and a constant value of reduced scattering ($\mu_s' = 1$ mm$^{-1}$). As the object gets deeper in the tissue, the optical properties of the tissue demonstrate an increasing influence on shaping the observed spectrum because of the increasing lightpaths traversed by light. The information contained in the distorted spectra may be distilled into a single quantity by calculating the ratio of the signal at two emission wavelengths, $$\Gamma = \frac{\psi^{em}(\vec{R},\lambda^{ex},\lambda_1)}{\psi^{em}(\vec{R},\lambda^{ex},\lambda_2)} \times \frac{\varepsilon_F^{em}(\lambda_2)}{\varepsilon_F^{em}(\lambda_1)} = \frac{G^{em}(\vec{R},\vec{r}_s,\delta^{\lambda_1},D^{\lambda_1})}{G^{em}(\vec{R},\vec{r}_s,\delta^{\lambda_2},D^{\lambda_2})} \quad \text{(Eqn. 4)}$$

where the intensity values at each wavelength are normalized with the relative signal strength of an undistorted emission spectrum, implying that $\Gamma$ should be equal to 1 for d=0 mm.

In Eqn. 4, $\Gamma$ is independent of the diffuse excitation field. This means that, in the point-source approximation limit, the ratio is independent of scattering and absorption of the stimulus light.

Inserting Eq. (2) into Eq. (4), we find that the logarithm of the fluorescence ratio for an infinite medium is linearly related to the depth in tissue of the fluorophores with a slope equal to the difference in penetration depth between wavelengths $\lambda_1$ and $\lambda_2$. This linear relationship can potentially be used in estimating depth from a simple measured ratio in the case of diffusive medium of infinite spatial extent. A more realistic model for epi-illumination imaging may also be obtained assuming there is an index of refraction mismatch boundary between tissue and air. The relationship obtained is then similar—up to a multiplicative factor—for depth values larger than approximately two millimeters. For smaller values than two millimeters, the relationship is non-linear.

An alternative embodiment superficially resembling that of FIG. 13 as heretofore described has a filter 1340 having a rotary disk with several bandpass elements. Each of the bandpass elements has a different center wavelength in the range of wavelengths emitted by a typical fluorescent material such as protoporphyrin IX, such as in the range 650-720 nanometers. In this embodiment, filter 1340 is a motorized, rotary, filter that successively rotates each bandpass element into an optical path of camera 1342. An image is captured by camera 1342 for each of the bandpass elements, such that the sequential images through different bandpass filters may be analyzed to determine spectra of received fluorescent light at each pixel of the image.

As described above with reference to Equations 1-4, the spectra of fluorescent light passing through tissue is altered by absorption and scattering in the tissue, such that spectra of the received fluorescent light 1336 encodes depth information. In an embodiment, two bandpass elements are used to derive a spectral deformation and depth for the fluorescent light captured in each pixel; in an alternative embodiment three or more bandpass elements are used to more precisely estimate spectral deformation due to passage of emitted light through tissue and thereby estimate depth for each pixel of the image.

In an embodiment, the depth information determined as described above, using modeling of scanned laser light 1346 and depth information derived from spectral information in received fluorescent light 1336, are used to provide a refined depth information, and to thereby provide a refined model of the tumor 1344. In an alternative mode of operating this embodiment, the scanning laser may be disabled and depth information derived solely from spectral deformation of fluorescent light stimulated by an appropriate flood illuminator.

In an embodiment using images recorded through two bandpass filters in the wavelength range of fluorescence in the fluorophores in tumor, a two dimensional table is used. This table is generated according to the optical properties of the tissue at the wavelengths of the bandpass filters as determined by measurement through imaging of scattering of a beam, or from a library of optical properties as previously discussed herein. This table is indexed by intensity at the higher wavelength bandpass filter in X, and intensity in the lower wavelength bandpass filter in Y, the table having entries of approximate depth of tumor based upon differences between intensity of fluorescent light passing the higher wavelength filter and the lower wavelength filter. The table is precomputed and stored in memory of the image processor to permit fast access. Intensity from each pixel in high wavelength and low wavelength images are used with a table interpolation algorithm as known in the art of computing to derive a depth associated with each pixel, and a three-dimensional model of fluorophore distribution is computed. Information from the model of fluorophore distribution is then displayed to the surgeon; this may be in the form of tomographic images, a topographic map, or by color coding of fluorescence magnitude with determined depth.

In another embodiment, the optical properties of the tissue as determined above at the wavelengths of the bandpass filter elements is used to compute the 'slope' for the log-linear relationship of the ratio of intensity at two wavelengths as described above with reference to substitution of Eqn. (2) into Eqn. (4). This 'slope' allows us relate the depth in tissue of the fluorophores to the difference in intensity between wavelengths $\lambda_1$ and $\lambda_2$. Then, the depth can be estimated based on the measured ratio:

$$d = \frac{\ln \Gamma - \ln \frac{D^{\lambda_2}}{D^{\lambda_1}}}{-\left[\frac{1}{\delta^{\lambda_1}} - \frac{1}{\delta^{\lambda_2}}\right]}, \quad \text{(Eqn. 5)}$$

Alternatively the more general expression associated with a semi-infinite diffusive medium may be used, as described above with reference to Eqn. 1-3.

An alternative embodiment 1402, as illustrated in FIG. 14, has two cooled CCD cameras 1404, 1406, each of which is equipped with a motorized rotary filter 1408, 1410. Each rotary filter 1408 has a series of at least two bandpass filters each having center frequency at different points in the range where fluorescent light is expected to be emitted by protoporphyrin IX, and a neutral-density filter for use in capturing white-light surface images. A separate rotary filter 1412 is provided for an optical path to eyepieces 1414, 1416 such that a surgeon has the option of viewing the tissue with and without fluorescent filtering while the cameras are using their bandpass filters to estimate depth. The microscope 1402 has a pair, or in an alternative embodiment, a single, objective lens or lenses 1420 which may be zoom lenses or may be an assortment of single or paired objective lenses mounted on a turret as known in the art of surgical and dissecting microscopes.

In this embodiment, light 1422 at a fluorescence stimulus wavelength, the light 1422 emitted by a fluorescence stimulus-wavelength emitter 1424, passes into tissue 1430 and tumor 1432. Such light 1442, 1444 as may be emitted by fluorophores in the tissue, and which diffuses to the surface of the tissue passes through the objective lenses 1420, through beamsplitters 1446, 1448, filter 1412 or other low-pass wavelength-selective device, and to the eyepieces 1414, 1416. A portion of light 1442, 1444 is diverted by the beamsplitters 1446, 1448 and through filters 1410, 1408 into the cameras.

Stimulus-wavelength emitter 1424 may be a light-emitting diode, a laser-diode, a scanned laser, a combination of a broadband source such as a halogen bulb and a filter, a combination of a broadband source with a filter and a light guide such as an optic fiber or fluid-filled light guide, a scanned laser, a laser with a diverging lens, or another device that is capable of providing substantial light 1422 at stimulus wavelength to tissue 1430 and tumor 1432 while providing substantially less or no light at fluorescence wavelength.

In this embodiment 1402, surface mapping may take place as heretofore described using neutral density filters at rotary filters 1410, 1408. During a fluorescence depth-resolving mode, two, or in an alternative embodiment three or more, bandpass filters at each of rotary filters 1410, 1408 are used to measure a wavelength distribution of received fluorescent light. In an embodiment, a depth is computed for each pixel using a table interpolation as heretofore described. In an alternative embodiment, three dimensional modeling of light diffusion is used to derive a three-dimensional model of fluorophore distribution in a manner similar to that previously discussed with reference to FIG. 4.

The embodiment 1402 may also be fitted with additional light sources, such as light source 1453, for providing illumination for other modes. For example, light source 1453 may be a white light emitting diode for use in a conventional white-light mode. Embodiment 1402 may also be fitted with a laser 1457 tunable across the wavelengths of fluorescent emissions and aimed to project a beam 1459 into the field of view at an angle. Prior to performing tomographic imaging, embodiments having laser 1457 may project beam 1459 into the tissue and image the beam as it penetrates, scatters and disperses in the tissue at the wavelengths of each bandpass filter of filters 1408, 1410. The image of the beam scattering in the tissue is used to determine optical properties of the tissue at each such wavelength, these optical properties are then used to build the tables for determining depth of fluorophores in the tissue or for modeling of propagation of light from fluorophores to determine fluorophore distribution in tissue.

Figure 15:
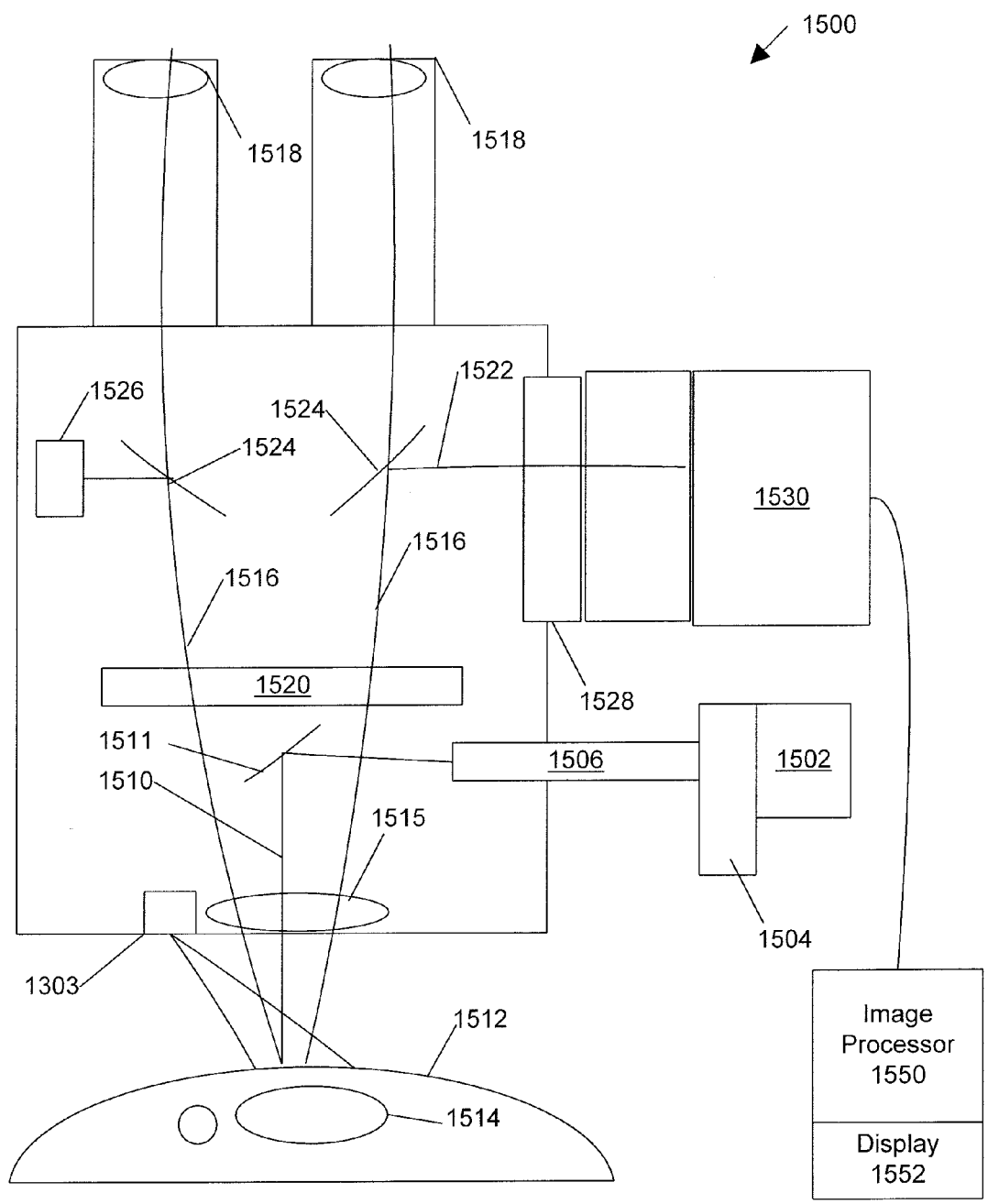
FIG. 15 illustrates an alternative embodiment based upon a modified commercial surgical microscope.

The embodiment of FIG. 15 is based upon a modified commercial surgical microscope such as the Leica® FL400 microscope system, Leica is a trademark of Leica Microsystems GMBH, Wetzlar, Germany for microscopes. In this embodiment, an external white-light source 1502 has an adjustable filter 1504 and a light pipe 1506 for bringing light into the microscope. There may be more than one such light source, filter, and light-pipe in various embodiments. Light 1510 from the light pipe is reflected by a mirror 1511 onto a surface of tissue 1512, where some of the light propagates to and illuminates tumor 1514. Light 1516 emitted by fluorescence in the tumor, and reflected and scattered light from tissue 1512 passes through one or two objective lenses 1515, a rotary observation filter assembly 1520 to eyepieces 1518, where it may be viewed by a surgeon.

In alternative embodiments, light source 1502 may be a light-emitting diode, a laser-diode, a laser, or an alternative white light source such as a gas-discharge lamp. The filter 1504 may be replaced with a dichroic mirror or a prism and slit, or other devices that can substantially reduce light at fluorescent wavelengths, and the light guide 1506 may be an optic fiber instead of the fluid-filled light guide of the Leica system described above.

In an ordinary observation mode, filter 1520 is a clear or neutral density filter, filter 1504 is a clear or neutral density filter, and the microscope operates conventionally.

In a fluorescence mode, filter 1520 is a low-pass filter that serves to block most light at stimulus wavelengths that is scattered and reflected by tissue 1512; and filter 1504 is a high-pass filter that blocks light from source 1502 such that little or no light at fluorescence wavelengths is passed to tissue 1512. Light 1516 emitted by fluorescence in tissue passes through filter 1520 and may be viewed by a surgeon through eyepieces 1518.

A portion 1522 of light 1516 is diverted by beamsplitters 1524 into an absorber 1526 or auxiliary eyepiece from one of two binocular pathways, through a motorized, rotary, filter 1528 in the other of the binocular pathways and into a cooled CCD camera 1530. Rotary filter 1528 has band-pass filter elements centered at each of several wavelengths in the range of wavelengths expected to be emitted by fluorophores in tissue 1512, and operates under control of image processor 1550 to allow CCD camera 1530 to capture images at each of these wavelengths. Image processor 1550 then in an embodiment executes a table interpolation to determine depth at each pixel of the images, or in an alternative embodiment executes a light-propagation modeling algorithm to create a three dimensional model of the fluorophore surface, and hence tumor 1514, in tissue.

In the embodiments illustrated in FIGS. 14 and 15, the three dimensional model of the tumor fluorophore surface in tissue is presented to the surgeon as previously discussed using a display device 1552. In embodiments resembling those illustrated in FIGS. 14 and 15, especially those using three or more bandpass elements, a three dimensional model of fluorophore distribution in tissue is constructed and presented to the surgeon as previously discussed using display device 1522. These embodiments may make use of a model of tissue surface derived from two white-light images as previously discussed to produce the three dimensional model of fluorophore distribution.

In an alternative embodiment based upon a different commercial surgical microscope system, the Zeiss OPMI Pentero®, a trademark of Carl Zeiss AG, Oberkochen, Germany, a dichroic mirror is used in place of both low-pass filter 1520 and mirror 1511. In this embodiment, fluorescent light from the tumor passes through the dichroic mirror to the CCD camera and eyepieces, while stimulus-wavelength light is reflected back into the light source. In this document, a filter such as filter 1520, and a dichroic mirror, are both low-pass wavelength-selective devices. Operation of most other portions of the system are as heretofore described.

In some embodiments a small cathode-ray tube or other display device may project color-encoded depth information directly into the optical path to eyepieces 1518 such that the surgeon may view depth information without having to look away from the surgical microscope and focus his eyes on a monitor.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A tomographic fluorescent imaging device for imaging fluorophores in biological tissues comprising:
   a light source configured to provide a beam of light, the beam of light having wavelength near a first stimulus wavelength;
   a scanner configured to scan the beam of light across biological tissues;
   a lens configured to collect light from the biological tissues, the light from the biological tissues being received at an angle to the beam of light;
   a first electronic camera system configured to capture a series of images, the series of images comprising stimulus wavelength images at a plurality of positions of the beam of light and fluorescence emission images at a plurality of positions of the beam of light, the fluorescence emission images captured using light at a second wavelength collected by the lens and passed by a first filter configured to block light of the first stimulus wavelength;
   at least a second optical electronic camera, the system being configured to generate a stereoscopic pair of images of the biological tissues using two electronic cameras, the two electronic cameras including the second electronic camera;
   an image processing system configured to compute a three-dimensional model of a surface of the biological tissues from the stereoscopic pair of images;
   wherein the image processing system is configured to use the three-dimensional model of the surface in constructing a model of transmission of the beam of light through the biological tissues;
   wherein the image processing system is configured to fit absorbance parameters of the model of transmission of the beam of light to the stimulus wavelength images;
   wherein the image processing system is further configured to derive images representing a three-dimensional distribution of fluorophore in the biological tissues from the series of fluorescence emission images by fitting fluorophore concentration parameters for each of a plurality of voxels of the model of transmission of the beam of light through the tissues to the fluorescence emission images, and generating tomographic images representing the three-dimensional distribution of fluorophore from the fitted fluorophore concentration parameters of the voxels of the model.

2. The imaging device of claim 1 wherein the first stimulus wavelength has a wavelength of at least six hundred nanometers.

3. The imaging device of claim 1 wherein the beam is a fan beam.

4. The imaging device of claim 1 wherein the beam is a spot beam.

5. The imaging device of claim 1 wherein the fluorescence emission images and the stimulus wavelength images are time resolved.

6. The imaging device of claim 1 further comprising a filter for blocking light of the first stimulus wavelength and passing light of the second wavelength, and wherein the fluorescence emission images are obtained from light passed through the filter.

7. The imaging device of claim 1, further comprising a monochromatic flood illuminator for inducing fluorescent light emission by fluorophores near a surface of the biological tissues, and a filter for blocking light from the monochromatic flood illuminator, the filter positioned in a light path between tissue and camera.

8. The imaging device of claim 1, further comprising a monochromatic flood illuminator of wavelength between six hundred and one thousand nanometers for inducing fluorescent light emission by fluorophores under the surface of the biological tissues, and a filter for blocking light from the monochromatic flood illuminator.

9. The imaging device of claim 1 further comprising a plurality of locator sensors for permitting a tracking computer to determine a location of the device.

10. The imaging device of claim 9 further comprising a coregistration computer for translating coordinates of the voxels from a fluorescence imaging coordinate system into a preoperative imagery coordinate system to superimpose fluorescence information of the voxels upon preoperative imagery, and for presenting superimposed images to a viewer.

11. The device of claim 10 further comprising a wand having a plurality of locator sensors for permitting the tracking computer to determine a location of the wand, and wherein the laser and the scanner are located in the wand.

12. The tomographic optical imaging device of claim 1 further comprising:
    a second light source for providing light around a third wavelength;
    wherein the first electronic camera is capable of capturing images of tissue illuminated by light of the first stimulus wavelength and light of the third wavelength;
    wherein the image processing system further models an absorbance parameter at the second wavelength, and determines an absorbance at the second wavelength at each voxel of the model of the tissue.

13. The imaging device of claim 1 wherein the first electronic camera system is configured with the first filter being a bandpass filter having a center wavelength within a wavelength band of fluorescence emission, and
    further comprises a second bandpass filter having a center wavelength within the wavelength band of fluorescent light at a wavelength different from the center wavelength of the first filter; and
    wherein the image processing system is configured to use ratios between intensity of fluorescent light from images recorded through the first and second bandpass filters to compute a depth of fluorophore distribution in the tissue.

14. The imaging device of claim 13 wherein the first and second filter are bandpass elements of a rotary filter.

15. The device of claim 14 further comprising at least a third bandpass element in the rotary filter, and wherein the image processing system computes depth of fluorophore in tissue based upon spectra of fluorescent light as imaged through the bandpass elements.

16. The device of claim 13 further comprising at least a second electronic camera, wherein the image processing system receives white-light images from the second and the third electronic cameras and computes a surface model of the biological tissues from the white light images, and wherein the image processing system computes a three dimensional model of fluorophore distribution in tissue based upon the surface model and the depth of fluorophore in issue.

17. The imaging device of claim 1 wherein the image processing system is configured for receiving the series of stimulus wavelength and fluorescence emission images,
    wherein the first electronic camera system is configured to capture the series of fluorescence emission images including at least one image captured with the light of the first stimulus wavelength entering tissue at at least a first location on the tissue, and at least another image captured with the light of the first stimulus wavelength entering tissue at at least a second location on the tissue;
    and wherein the image processing system is configured for computing an illumination at voxels of a model of light transmission through the tissue for each of the positions of the beam, and for determining a fluorescence emission at each voxel of the model of the tissue.

18. The tomographic fluorescent imaging device of claim 1 wherein the image processing system is further configured to provide tomographic images of a degree of oxygenation in tissue.

19. The tomographic fluorescent imaging device of claim 1 wherein the absorbance parameters are used in the model of transmission of the beam of light through the tissues while fitting the fluorophore concentration to the fluorescence emission images.

20. The tomographic fluorescent imaging device of claim 1 wherein the tomographic images are derived from intersections of a sequence of planes with the three-dimensional model of fluorophore distribution.

* * * * *